United States Patent
Waldman et al.

(10) Patent No.: US 9,429,576 B2
(45) Date of Patent: *Aug. 30, 2016

(54) COMPOSITIONS AND METHODS FOR IDENTIFYING AND TARGETING CANCER CELLS OF ALIMENTARY CANAL ORIGIN

(71) Applicant: Thomas Jefferson University, Philadelphia, PA (US)

(72) Inventors: Scott A. Waldman, Ardmore, PA (US); Jason Park, Philadelphia, PA (US); Stephanie Schulz, West Chester, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/520,962

(22) Filed: Oct. 22, 2014

(65) Prior Publication Data

US 2015/0104382 A1   Apr. 16, 2015

Related U.S. Application Data

(60) Continuation of application No. 13/277,612, filed on Oct. 20, 2011, now Pat. No. 8,946,168, which is a division of application No. 12/961,373, filed on Dec. 6, 2010, now Pat. No. 8,067,007, which is a division of application No. 10/866,951, filed on Jun. 14, 2004, now Pat. No. 7,854,933, which is a division of application No. 09/819,249, filed on Mar. 27, 2001, now Pat. No. 6,767,704.

(60) Provisional application No. 60/192,229, filed on Mar. 27, 2000.

(51) Int. Cl.

| | |
|---|---|
| *A61K 39/395* | (2006.01) |
| *A61K 9/127* | (2006.01) |
| *G01N 33/574* | (2006.01) |
| *A61K 31/7034* | (2006.01) |
| *A61K 31/7048* | (2006.01) |
| *C12Q 1/68* | (2006.01) |
| *A61K 47/48* | (2006.01) |
| *A61K 51/10* | (2006.01) |
| *C07K 16/40* | (2006.01) |

(52) U.S. Cl.

CPC ..... *G01N 33/57446* (2013.01); *A61K 31/7034* (2013.01); *A61K 31/7048* (2013.01); *A61K 47/48646* (2013.01); *A61K 51/1075* (2013.01); *C07K 16/40* (2013.01); *C12Q 1/6886* (2013.01); *G01N 33/57407* (2013.01); *G01N 33/57419* (2013.01); *C12Q 2600/158* (2013.01); *G01N 2333/988* (2013.01)

(58) Field of Classification Search

None
See application file for complete search history.

(56) References Cited

U.S. PATENT DOCUMENTS

| | | |
|---|---|---|
| 4,022,878 A | 5/1977 | Gross |
| 4,329,281 A | 5/1982 | Christenson et al. |
| 4,341,763 A | 7/1982 | Zygraich |
| 4,526,716 A | 7/1985 | Stevens |
| 4,584,268 A | 4/1986 | Ceriani et al. |
| 4,601,896 A | 7/1986 | Nugent |
| 4,659,666 A | 4/1987 | May et al. |
| 4,729,893 A | 3/1988 | Letcher et al. |
| 4,736,866 A | 4/1988 | Leder et al. |
| 4,849,227 A | 7/1989 | Cho |
| 4,867,973 A | 9/1989 | Goers et al. |
| 4,873,191 A | 10/1989 | Wagner et al. |
| 4,945,050 A | 7/1990 | Sanford et al. |
| 4,963,263 A | 10/1990 | Kauvar |
| 4,965,188 A | 10/1990 | Mullis et al. |
| 5,000,935 A | 3/1991 | Faulk |
| 5,017,487 A | 5/1991 | Stunnenberg et al. |
| 5,037,645 A | 8/1991 | Strahilevitz |
| 5,075,216 A | 12/1991 | Innis et al. |
| 5,087,616 A | 2/1992 | Myers et al. |
| 5,112,606 A | 5/1992 | Shiosaka et al. |
| 5,133,866 A | 7/1992 | Kauvar |
| 5,140,102 A | 8/1992 | Currie |
| 5,143,854 A | 9/1992 | Pirrung et al. |
| 5,160,723 A | 11/1992 | Welt et al. |
| 5,166,320 A | 11/1992 | Wu et al. |
| 5,217,869 A | 6/1993 | Kauvar |
| 5,221,736 A | 6/1993 | Coolidge et al. |
| 5,223,409 A | 6/1993 | Ladner et al. |
| 5,237,051 A | 8/1993 | Garbers et al. |
| 5,252,743 A | 10/1993 | Barrett et al. |

(Continued)

FOREIGN PATENT DOCUMENTS

| | | |
|---|---|---|
| EP | 0846949 A1 | 6/1998 |
| EP | 10922738 | 2/2003 |
| WO | 9011092 A1 | 10/1990 |
| WO | 9214470 A1 | 9/1992 |
| WO | 9511694 A1 | 5/1995 |
| WO | 9742220 A1 | 11/1997 |
| WO | 9742506 A1 | 11/1997 |
| WO | 9841864 A1 | 9/1998 |
| WO | 9907726 A1 | 2/1999 |
| WO | 0020640 A1 | 4/2000 |
| WO | 0173132 A1 | 10/2001 |
| ZA | 839512 | 12/1998 |

OTHER PUBLICATIONS

Debruyne et al, Expert Opinion Pharmacotherap., 2003, 4:1083-1096.*

(Continued)

*Primary Examiner* — Laura B Goddard

(74) *Attorney, Agent, or Firm* — Pepper Hamilton LLP

(57) ABSTRACT

Screening and diagnostic reagents, kits and methods for primary and or metastatic stomach or esophageal cancer are disclosed. Compositions for and methods of imaging and treating primary and/or metastatic stomach or esophageal cancer are disclosed. Vaccines compositions and methods of for treating and preventing primary and/or metastatic stomach for esophageal cancer are disclosed.

18 Claims, No Drawings

(56) References Cited

U.S. PATENT DOCUMENTS

| | | | |
|---|---|---|---|
| 5,270,170 A | 12/1993 | Schatz et al. | |
| 5,271,961 A | 12/1993 | Mathiowitz et al. | |
| 5,288,514 A | 2/1994 | Ellman | |
| 5,324,483 A | 6/1994 | Cody et al. | |
| 5,330,892 A | 7/1994 | Vogelstein et al. | |
| 5,338,665 A | 8/1994 | Schatz et al. | |
| 5,340,474 A | 8/1994 | Kauvar | |
| 5,350,741 A | 9/1994 | Takada | |
| 5,352,775 A | 10/1994 | Albertsen et al. | |
| 5,366,862 A | 11/1994 | Venton et al. | |
| 5,384,261 A | 1/1995 | Winkler et al. | |
| 5,395,750 A | 3/1995 | Dillon et al. | |
| 5,399,347 A | 3/1995 | Trentham et al. | |
| 5,405,783 A | 4/1995 | Pirrung et al. | |
| 5,412,087 A | 5/1995 | McGall et al. | |
| 5,420,328 A | 5/1995 | Campbell | |
| 5,424,186 A | 6/1995 | Fodor et al. | |
| 5,430,138 A | 7/1995 | Urdea et al. | |
| 5,437,977 A | 8/1995 | Segev | |
| 5,443,816 A | 8/1995 | Zamora et al. | |
| 5,489,670 A | 2/1996 | Currie et al. | |
| 5,518,888 A * | 5/1996 | Waldman | A61K 47/48238 424/1.69 |
| 5,585,479 A | 12/1996 | Hoke et al. | |
| 5,593,825 A | 1/1997 | Carman et al. | |
| 5,601,990 A | 2/1997 | Waldman | |
| 5,731,159 A | 3/1998 | Waldman | |
| 5,879,656 A | 3/1999 | Waldman | |
| 5,957,909 A | 9/1999 | Hammons et al. | |
| 5,962,220 A | 10/1999 | Waldman | |
| 5,969,097 A | 10/1999 | Wiegand et al. | |
| 6,060,037 A | 5/2000 | Waldman | |
| 6,130,043 A | 10/2000 | Billing-Medel et al. | |
| 6,602,659 B1 | 8/2003 | Waldman et al. | |
| 8,946,168 B2 | 2/2015 | Waldman et al. | |
| 2004/0258687 A1 | 12/2004 | Waldman et al. | |
| 2005/0287067 A1 | 12/2005 | Wolfe et al. | |

OTHER PUBLICATIONS

Park et al (Cancer Epidemiology, Biomarkers & Prevention, 2002, 11:739-744).*
Smith et al., "A ribonuclease S-peptide antagonist discovered with a bacteriophage display library", Gene, 1993, 128, 37-42.
Tucker, K. et al., "Covalent Attachment of Chelating Groups to Macromolecules", Biochem. Biophys. Res. Commun., 1977, 77(2), 581-585.
Vandraager A. et al., "Guanylyl Cyclase C is an—Linked Glycoproein Receptor that Accounts for Multple Heat-stabe Enterotoxn-binding Proteins in the Intestine", J. Biol. Chem., 1993, 268(3), 2174-2179.
Wang et al., "Application of the Multipin Peptide Synthesis Technique for Peptide Receptor Binding Studies: Substance P as a Model System", Bioorg. Med. Chem. Lett., 1993, 3(3), 447-450.
Zuckermann et al., "Discovery of Nanomolar Ligands for 7-Transmembrane G-Protein-Coupled Receptors from a Diverse N-(Substituted)glycine Peptoid Library", J. Med. Chem., 1994, 37, 2678-2685.
Eildon, S.P., "Cytotoxicity and viability assays", Animal Cell Culture: A Practical Approach, Freshney, R.I. (Ed.), IRL Press, Oxford, 1986, 183-216.
Sad, S., et al., "Bypass of carrier-induced epitope-specific suppression using a T-helper epitope," Immunology, 1992, 76, 599-603.
Aimoto S., et al., "Chemical synthesis of a highly potent and heat-stable analog of an enterotoxin produced by a human strain of enterotoxigenic *Escherichia coli*," Biochem. & Biophy. Res. Comm., 1983, 112(1), 320-326.
Carepick, B.W., et al., "The *Escherichia coli* heat-stable enterotoxin is a long-lived superagonist of guanylin," Infection & Immunity, 1993, 61(11), 4710-4715.
Gariepy, J., "Importance of disulfide bridges in the structure and activity of *Escherichia coli* enterotoxin St1b," Proc. Natl. Acad. Sci. USA, 1987, 84, 8907-8911.

Hidaka, Y., e tal., "Disulfide linkages in a heat-stable enterotoxin (Stp)poduced by a porcine strain of enterotoxgenic *Escherichia coli*," Bull. Chem. Soc. Jpn., 1988, 61, 11265-1271.
Ikemura, H., et al., "Heat-stable enterotoxin ($ST_h$) of human enterotoxigenic *Escherichia coli* (Strain SK-1). Structure-activity relationship," Chem. Soc. of Jpn., 1984, 57(9), 2150-2156.
Ikemura, H., et al., "Synthesis of a heat-stable enterotoxin($ST_h$) poduced by a human strain SK-1 enterotoxigenic *Escherichia coli*," Chem. Soc. of Jpn., 1984, 57, 2543-2550.
Kubota, H., et al., "A long-acting heat-stable enterotoxin analog of enterotoxigenic *Escherichia coli* with a single D-amino acid," Biochem. & Biophy. Res., 1989, 161(1), 229-235.
Yoshimura, S., Chemical synthesis of a heat-stable enterotoxin produced by enterotoxigenic *Escherchia coli* strain 18D. Chem. Soc. Jpn., 1984, 125-133.
Yoshimura, S., et al., "A heat-stable enterotoxin of vibrio cholerae non-01: chemical synthesis, and biological and physicochemical properties," Biopolymers, 1986, 25, S69-S83.
Sizeland, A.M., et al "Anti-sense transforming growth factor alpha oligonucleotides inhibit anutocrine stimulated proliferation of a colon carcinoma cell line," Moecular Biology of the Cell, 1992, 3, 1235-1243.
MacLean, G.D., et al., "Immunization of breast cancer patients using a synthetic sialyl-Tn glycoconjugate plus detox adjuvant," Cancer Immunol. Immunother, 1993, 36, 215-222.
Maier, A., et al., "Effect of photodynamic therapy in a multimodal appreach for advanced carcinoma of the gastro-esophageal junction," Lasers in Surgery and Medicine, 2000, 26, 461-466.
Miller, S.D., et al., "The induction of hapten-specific T cell tolerance by using hapten-modified lymphoid cells," J. Immunol., 1976, 117(5:1), 1519-1526.
U.S. Appl. No. 08/468,449, Waldman, filed Jun. 6, 1995.
PCT International Search Report dated Aug. 7, 1997, 1 page.
The EPO Supplementary Partial European Search Report dated Feb. 28, 2003 (EP 01 92 2738).
Bold et al., "Experimental Gene Therapy of Human Colon Cancer," Surgery (1994) 116(2):189-196.
Giardiello et al., "Inhibition of Cripto Expression and Tumorigenicity in Human Colin Cancer Cells by Antisense RNA and Oligodoxynucleotides," (1994) Oncogene 9(1):291-298.
The Proteins, vol. II, 3rd Ed., Neurath et al. (eds), Academic Press, New York, NY, pp. 105-237.
Birbe et al., "Guanylyl cyclase C is a marker of intestinal metaplasia, dysplasia, and adenocarcinoma of the gastrointestinal tract," Human Pathology (2005) 36(2):170-179.
Waldman et al., "Use of guanylyl cyclase c for detecting micrometastases in lymph nodes of patients wth colon cancer" Diseases of the Colon and Rectum (1998) 41(3):310-315.
In re Alonso, Oct. 2008, U.S. Court of Appeals for the Federal Circuit (pp. 1-11 + cover).
Debuyne et al., "Pathological staging and therapy of oesophageal and gastric cancer," Expert Opinion Pharmacotherap. (2003) 4:1083-1096.
Park et al., "Ectopic expression of guanylyl cyclase C in adenocarcinomas of the esophagus and stomach," Cancer Epidemiology, Biomarkers & Prevention (2002) 11(8):739-744.
White et al., "Antibody-targeted immunotherapy for treatment of malignancy," Ann Rev Med (2001) 52:125-145.
Topp et al., "Antibody transport in cultured tumor cell layers," Journal of Controlled Release (1998) 53(1-3):15-23.
Fava et al., "Ectopic expession of guanylyl cyclase C in CD34+ pogenitor cells in peripheral bloo" Journal of Clinical Oncology (2001) 19(19:3951-3959.
Behrends et al., "The beta(2) subunit of soluble guanylyl cyclase contains a human-specific frameshift and is expressed in gastric carcinoma," Biochemical and Biophysical Research Communications (2000) 271(1):64-69.
Wide, "Solid phase antigen-antibody systems," Radioimmunoassay Methods, Kirkham (Ed.), E & S pp. 405-412. Livingstone, Edinburough, 1971.
Aitken, R. et al., "Recombinant enterotoxins as vaccines against *Escherichia coli*-mediated diarrhoea", Vaccine, 1993, 11(2) 227-233.

(56) References Cited

OTHER PUBLICATIONS

Field, M., "Role of Cyclic Nucleotides in Enterotoxic Diarrhea", Mol. Cyclic Nucl. Res., 1980, 12, 267-277.
Giannella, R.A., "Pathogenesis of Acute Bacterial Diarrheal Disorders", Ann. Rev. Med., 1981, 32, 341-357.
Rao, M.C. et al., "Enterotoxins and Anti-toxins: Enterotoxins and ion transport", Biochem., 1984, 12, 177-180.
Chelly, J., et al., "Illegitimate transcription: Transcription of any gene in any cell type," Proc. Natl. Acad. Sci. USA, 1989, 86, 2617-2621.
Chelly, J., et al., "Illegitimate transcription: application to the analysis of truncated transcripts of the dystrophin gene in nonmuscle cultured cells from duchenne and becker patients," J. Clin. Invest., 1991, 88(4), 1161-1166.
Cooper, D.N., et al., "Ectopic (Illegitimate) transcrption: new possibilities for the analysis and diagnosis of human genetic disease," Ann. Med., 1994, 26(1), 9-14.
Kaplan, J.C., et al., "Illegitimate transcription: its use in the study of inherited disease," Human Mutation, 1992, 1(5), 357-360 (Abstract only).
Negrier C., et al., "Illegitimate transcription: its use for studying genetic abnomalites in lymphoblastoid cells from patients with glanzmann thrombasthenia," British J. Haematology, 1998, 100(1), 33-39.
Zippelius, A., et al., "Limitations of reverse-transcriptase polymerase chain reaction analyses for detection of micrometastatic epithelial cancer cells in bone marrow," J. Olin. Oncology, 1997, 15(7), 2701-2708.
Carrithers et al., "Guanylyl cyclase C is a selective marker for metastatic colorectal tumors in human extraintestinal tissues", Proc. Natl. Acad. Sci. USA, 1996, 93, 14827-14832.
Carrithers et al., "*Escherichia coli* Heat-Stable Toxin Receptors in Human Colonic Tumors", Gastroenterology, 1994, 107, 1653-1661.
Hugues et al., Affinity Purification of Functional Receptors for *Escherichia coli* Heat-Stable Enterotoxin.
Urbanski et al., "Internalization of *E. coil* ST mediated by guanylyl cyclase C in T84 human colon carcinoma cells", Biochim. Et Biophys. Acta, 1995, 1245, 29-36.
Orkin et al., "Report and Recommendatons of the Panel to Assess the NIH Investment in Research on Gene Theapy", p. 41, Dec. 1995.
Ciardiello, F. et al., "Inhibition of CRIPTO Expression and Tumorigenicity in Human Colon Cancer Cells by Antisense RNA and Oligodeoxynucleotides", Oncogene, 1994, 9(1), 291-298.
Paxon, R. et al., "High-Specific-Activity Labeled Anticarcinornembryonic Antigen Monoclonal Antibody: Improved Method for the Synthesis of Diethylenetriarninepentaacetic Acid Conjugates", Cancer Res., 1985, 45, 5694-5699.
Alexander, R.J. et al., "Oncogene Alterations in Rat Colon tumors Induced by—methyl-N-nitrosourea", Am. J. Med. Sci., 1992, 303(1), 16-24.
Collins, J.F. et al., "C-myc Antisense Oligonucleotides Inhibit the Colony-forming Capacity of Colo 320 Colonic Carcinoma Cells", J. Clin. Investigation, 1992, 89(5), 1523-1527.
Cooney, M. et al., "Site-Specific Oligonucleotide Binding Represses Transcription of the Human c-myc Gene in Vitro", Science, 1988, 241, 456-459.
Dayhoff, M.D., "Atlas of Protein Sequence and Structure", Nat Biomed. Res. Found., 1978, vol. 5, Supp. 3, Washington, D.C.
Heene, C. and Toulme, "Specfic Regulation of Gene Expesson by Antisense and Antigene Nucleic Acids", Biochem. Biophys. Acta, 1990, 1049, 99-125.
Kent, S. and Clark-Lewis in "Synthetic Peptides in Biology and Medicine", Alitalo, K. et al. (eds.), Science Publishers, Amsterdam, 1985, pp. 29-57.
Knyazev, P.G. et al., "Complex Characteristics of the Alterations of Oncogenes HER-2/ERBB-2. HER-1/ERBB-1, HRAS-1, C-MYC and Anti-Oncogenes p53, RB1, as well as Deletions of Loci of Chromosome 17 in Colon Carcinoma", Molekuliamaia Biologiia, 1992,26(5), 1134-1147 (English translation).
Melani, C. et al. "Inhibition of Proliferation by c-myb Antisense Oligodeoxynucleotides in Colon Adenocarcinoma Cell Lines that Express c-myb", Cancer Res., 1991, 51(1), 2897-2901.
Nielsen, P.E. et al., "Sequence-specific Transcription Arrest by Peptide Nucleic Acid Bound to the DNA Template Strand" Gene, 1994, 149, 139-145.
Ramsay, R.G. et al., "Myb Expression is Higher in Malignant Human Colonic Carcinoma and Premalignant Adenomatous Polyps than in Normal Mucosa", Cell Growth & Differentiation, 1992, 3(10), 723-30.
Rodriguez-Alfageme, C. et al., "Suppression of Deregulated c-MYC Expression in Human Colon Carcinoma Cells by Chromosome 5 Transfer", PNAS USA, 1992, 89(4), 1482-1486.
Ullrich, A., et al., "Insulin-like growth factor I receptor primary structure: comparison with insulin receptor suggests structural determinants that define functional specificity," EMBO J., 1986, 5(10), 2503-2512.
Tanaka, K. et al., "Suppression of Tumorigenicity in Human Colon Carcinoma Cells by Introduction of Normal Chromosome 1p36 Region", Oncogene, 1993, 8(8), 2253-2258.
Takekawa, M. et al., "Chromosomal Localization for the Protein Tyrosine Phosphatase G1 Gene and Characterization of the Aberrant Transcripts in Human Colon Cancer Cells", FEBS Letters, 1994, 339(3), 222-228.
Toribara, N.W. and Sleisenger, "Screening for Colorectal Cancer", New England J. Med., 1995, 332, 861-867.
Yokozaki, H. et al., "An Antisense Oligodeoxynuiceotide that Depletes R1 Alpha Subunit of Cyclic AMP-dependent Protein Kinase Induces Growth Inhibition in Human Cancer Cells", Cancer Research, 1993, 53(4), 868-872.
Beck-Sickinger et al., "Neuropeptide Y: identification of the binding site", Int. J. Peptide Protein Res., 1990, 36, 522-530.
Blond-Elguindi et al., "Affinity Panning of a Library of Petides Displayed on Bacteriophages Reveals the Binding Specificity of BiP", Cell, 1993.
Bremer, K,H. et al., "Safety and Efficacy of Radiopharmaceuticals," Kristensen, K. (eds.), Martinus Nijhoff Publishers, Dordrecht, The Netherlands, 1987, 43-50.
Cull et al., "Screening for receptor ligands using large libraries of peptides linked to the C terminus of the lac repressor", Proc. Natl. Acad. Sci. USA, 1992, 89, 1865-1869.
DeVita, V., "Principles of Cancer Therapy" in Harrison's Principle of internal Medicine, McGraw-Hill, New York, 1983, 765-787.
Fodor, S., "Light-Directed, Spatially Addressable Parallel Chemical Synthesis", Science, 1991, 251, 767-773.
Gallop et al., "Applications of Combinatorial Technolodies to Drug Discovery. 1. Backgound and Peptide Combinatorial Libraries", J. Med. Chem., 1994, 37(9), 1233-1251.
Gordon et al., "Applications of Combinatorial Technologies to Drug Discovery. 2. Combinatorial Organic Synthesis, Library Screening Strategies, and Future Directions", J. Med. Chem., 1994, 37(10), 1385-1401.
Hammer et al., "Promiscuous and Allele-Specific Anchors in HLA-DR-Binding Peptides", Cell, 1993, 74, 197-203.
Hamra, F. et al., "Uroguanylin: Structure and Activity of a Second Endogenous Peptide that Stimulates Intestinal Guanylate Cyclase", PNAS USA, 1993, 90, 10464-10468.
Kite, T. et al., "Characterization of Human Uroguanylin: a Member of the Guanylin Peptide Famiiy", Am. J. Physiol., 1994, 266, F342-F348.
Ohlmeyer et al., "Complex synthetic chemical libraries indexed with molecular tags", Proc. Natl. Acad. Sci. USA, 1993, 90, 10922-10926.
Osteresh et al., "Libraries from libraries": Chemical transformation of combinatorial libraries to extend the range and repertoire of chemical diversity, Proc. Natl. Acad. Sci. USA, 1994, 91, 11138-11142.
Ruggeri et al., "Inhibition of platelet functon wth synthetic peptides designed to be high-affinity antagonists of fibrinogen binding to platelets", Proc. Natl. Acad. Sci. USA, 1986, 83, 5708-5712.
Sepetov et al., "Library of libraries: Approach to synthetic combinatorial library design and screening of "pharmacophore" motifs", Proc. Natl. Acad. Sci. USA, 1995, 92, 5426-5430.

(56) References Cited

OTHER PUBLICATIONS

Chan, et al., "Amino acid sequence of heat-stable enterotoxin produced by *Escherchia coli* pathogenic for man" J. Biol. Chem., 1981, 256, 7744-7746.
Chung, et al., "Enzymatically active peptide from the adenosine diphosphate-ribosylating toxin of pseudomonas aeruginosa," Infection and Immunity, 1997, 16, 832-841.
Cumber, et al., "Preparation of antibody-toxin conjugates," Methods in Enzymology, 1985, 112, 207-225.
Currie, et al., "Guanylin: An endogenous activator of intestinal guanylate cyclase," Proc. Natl. Acad. Sci. USA, 1992, 89, 947-951.
Dreyfus, et al. "Chemical properties of heat-stable enterotoxins produced by enterotoxigenic *Escherichia coli* of different host origins," Infection and Immunity, 1983, 42, 539-548.
Eckelman, et al., Nucl. Med. Biol., 1986, 14.
Evans, et al., "Differences in the response of rabbit small intestine to heat-labile and heat-stable enterotoxins of *Escherichia coli*," Infection and Immunity, 1973, 7, 873-880.
Fitzgerald, et al., "Adenovirus-induced release of epidermal growth factor and pseudomonas toxin into cytosol of KB cells during receptor-mediated endocytosis," Cell, 1983, 32, 607-617.
Fitzgerald, "Construction of immunotoxins using pseudomonas exotoxin A," Methods in Enzymology, 1987, 151, 139-145.
Giannella et al., "Development of a radioimmunoassay for *Escherichia coli* heat-stable enterotoxin: Comparson with the suckling mouse bioassay," Infection and Immunity, 1981, 33, 186-192.
Waldman, S.A., et al., "Immunoaffinity purification of soluble guanylyl cyclase," Methods of Enzymol., 1991, 195, 391-396.
Hugues, et al., "Identification and characterization of a new famiy of high-affinity receptors for *Escherichia coli* heat-stable enterotoxin in rat intestinal membranes," Biochemistry, 1991, 30, 10738-10745.
Humm, et al., "Dosimetric aspects of radiolabeled antibodies for tumor therapy," J. Nuclear Med., 1986, 27, 1490-1497.
Klipstein, et al., "Development of a vaccine of cross-linked heat-stable and heat-liable enterotoxins that protects against *Escherichia coli* producing either enterotoxin," Infection and Immunty, 1982, 37, 550-557.
Krecarek, et al., "Covalent attachment of chelating groups macromolecules," Biochemical and Biophysical Res. Comm., 1977, 77, 581-585.
Chabalgoity, et al., "Expression and immunogenicity of an echinococcus granulosus fatty acid-binding protein in live attenuated *Salmonella* vaccine strains." Infection and immunity, 1997, 65(60), 2402-2412.
Karem, et al., "Differential induction of carrier antigen-specific immunity by *Salmonella typhimurium* live-vaccine strains after single mucosal or intravenous immunization of balb/c mice," Infection and Immunity, 1995, 63(12), 4557-4563.
O'Callaghan, et al., "Immune responses in balb/c mice following immunization with aromatic compound or purine dependent *Salmonella typhimurimun* strains," Immunology. 1990. 69(2), 184-189.
Mann, E.A., et al., "Comparison of freceptors for *Escherichia coli* heat-stable enterotoxin: novel receptor present in IEC-6 cells," Am. J. Physiol., 1993, 264, G172-G178.
Berd, D., et al., "Induction of cell-mediated immunity to autologous melanoma cells and regression of metastases after treatment with a melanoma cell vaccine proceded by cyclophsphamide," Cancer Research, 1986, 46, 2572-2577.
Bard, D., et al., "Immunization with haptenized, autologous tumor cells induced inflammation of human melanoma metastases," Cancer Research, 1991, 51, 2731-2734.
DeVita, V.T., Jr. in "Harrison's Principles of Internal Medicine," McGraw-Hill Book Co., NY, 1983, p. 68.
Francis, M.J. et al., "Peptide vaccines based on enhanced immunogenicity of peptide epitopes presented with T-cell determinants or hepatisis B core protein," Methods of Enzymol., 1989, 178, 659-676.

Haralambidis, J., et al., "The solid phase synthesis of oligonucleotides containing a 3'-peptide moiety," Tetrahedron Lett., 1987, 28(43), 5199-5202.
Mallo, G.V., et al., "Molecular cloning, sequencing and expression of the mRNA enclding human Cdx1 and Cdx2 homeobox. Down-regulation of Cdx1 and Cdx2 mRNA expression during colorectal carcinogenesis," Int. J. Cancer (Pred. Oncol), 1997, 74, 35-44.
Wu, G.D., et al., "Sucrase-isomaltase gene expression in barrett's esophagus and adenocarcinoma," Gastroenterology, 1993, 105, 837-844.
Cagir, B., et al., "Guanylyl cyclase C messenger RNA is a biomarker for recurrent stage II colorectal cancer," Am. Soc. Internal Med., 1999, 131(11), 805-812.
Li,Z., et al., "Peptide-regulated guanylate cyclase pathways in rat colon: in situ localization of GCA, GCC, and guanylin mRNA," Am. Physiologcal Soc., 1993, G394-G402.
London, R.M., et al., "Signal transduction pathways via guanylin and uroguanylin in stomach and intestine," Am. Physiological Soc., 1997, G93-G105.
Mallo, G.V., et al., "Expression of the Cdx1 and Cdx2 homeotic gene leads to reduced malignancy in colon cancer-derived cells," J. Biological Chem., 1998, 273(22), 14030-14036.
Corstens, et al., "Chemotactic peptides: New locomotion for imaging infection?." J. Nucl. Med., 1991, 32(3), 491-494.
Thompson, "*Escherichia coli* heat-stable enterotoxins and their receptors," Pathol. Immunopathol. Res., 1987, 6, 103-116.
Fischman, et al., "A ticket to ride: peptide radiopharmaceuticals," J. Nucl. Med., 1993, 34, 2253-2263.
Cohen, M., et al., "Receptors for *Escherichia coli* heat stable enterotoxin in human inestine and in a human intestinal cell line (Caco-2)," J. Cellular Physiol., 1993, 156, 138-144.
Guarino, A., et al., "T.sup.84 cell receptor binding and guanyl cyclas activation by *Escherichia coli* heat-stable toxin," Am. J. Physiol., 1987, 253 (Gastroinest. Liver Physiol. 16), G775-780.
Vaandrager, A., et al., "Atriopeptines and *Escherichia coli*, enterotoxin .sup.Sta have different sites of action in mammalian intestine," 1991, 102(4), 1161-1169.
De Sauvage, F., et al., "Primary structure and functional expression of the human receptor for *Escherichia coli* heat-stable enterotoxin," J. Biol. Chem., 1991, 266, 17912-17918.
Franz, et al., "The production of 99m TC-labeled conjugated antibodies using a cyclam-based bifunctional chelating agent," J. Nucl. Med. Biol., 1987, 14, 589-572.
Eckelman, et al., "Comparison of TC and in labeling of conjugated antibodies," Nucl. Med. Biol., 1986, 13, 335-343.
Gros, O., "Biochemical aspects of immunotoxin preparation," J. Immunol. Meth., 1985, 81, 283-297.
Gyles, C.L., "Discussion: heat-labels and heat-stable forms of the enterotoxin form *E. coli* strains enteropathogenic for pigs," Ann N.Y. Acad. Sci., 1979, 16, 314-321.
Hakki, et al., "Solubilization and characterization of functionally coupled *Escherichia coli* heat-stable toxin receptors and particulate guanylate cyclase associated with the cytoskeleton compartment of intestinal membranes," Int. J. Biochem., 1993, 25, 557-566.
Wide, "Radioimmune Assay Method," Kirkham (Ed.), E & S. Livingstone, Edinburgh, 1970, 199-206.
Richardson, et al., "Astatine(211 AT) as a therapeutic radionuclide, The plasma: blood cell distribution in vitro," Nucl. Med. Biol., 1986 13, 583-584.
Almenoff, et al., "Ligand-based histochemical localization and capture of cells expressing heat-stable enterotoxin receptors," Molecular Microbiology, 1993, 8, 865-873.
Bjorn, et al., "Antibody-pseudomonas exotoxin A conjugates cytotoxic to human breast cancer cells in vitro," Cancer Research, 1986, 46, 3262-3267.
Bjorn, et al., "Evaluation of monoclonal antibodies for the development of breast cancer immunotoxins,"Cancer Research, 1985, 45, 1214-1221.
Bodansky, et al., "Peptide synthesis," John Wiley and Sons, 2.sup.nd Ed., 1976.
Burgess, et al., "Biological evaluation of a methonal-soluble, heat-stable *Escherichla coil* enterotoxin in infant mice, pigs, rabbits, and calves,"Infection and immunity 21, 1978, 526-531.

(56) References Cited

OTHER PUBLICATIONS

Cawley, et al., "Epidermal growth factor-toxin a chain conjugates: EGF-Ricin A is a potent toxin while EGF-Diptheria Fragment A is nontoxic," Cell, 1980, 22, 563-570.
London R M et al., "Signal transduction Pathways via Guanylin and Uroguanylin in Stomach and Intestine" American Journal of Physiology; Gastrointesinal and Liver Physiology, American Physiological Society, US, 1997, pp. G93-G105, XP002943296; ISSN: 0193-1857.
Bustin S A et al. "Detection of Cytokeratins 19/20 and Guanylyl Cyclase C in Peripheral Blood of Colorectal Cancer Patients" British Journal of Cancer, London, GB, vol. 79, No. 11/12, Apr. 1999, pp. 1813-1820, XP00949369, ISSN: 0007-0920.
Kwok, "Calculation of radiation doses for nonuniformly distributed .beta. and .gamma. radionuclides in soft tissue," Med. Phys., 1985, 12, 405-412.
Leonard, et al. "Kinetics of protein synthesis inactivation in human T-lymphocytes by selective monoclonal antibody-ricin conjugates," Cancer Res., 1985, 5263-5269.
Masuho, et al., "Importance of the antigen-binding valency and the nature of the cross-linking bond in ricin A-chain conjugates with antibody," J. Biochem., 1982, 91, 1583-1591.
Merrifield, "Solid phase peptide synthesis. 1. The synhesis of a tetrapeptide" J. Am. Chem. Soc., 1963, 15, 2149-2154.
Michel, et al., "Fluorescence studies of nucleotides binding to diphtheria toxin and its fragment A," Biochimica et Biophysia Acta, 1974, 365, 15-27.
Moseley, et al., "Isolation and nucelotide sequence determination of a gene encoding a heat-stable enterotoxin of *Escherichia coli*," Infection and Immunity, 1983, 39, 1167-1174.
Okamoto, et al., "Substitutions of cystein residues of *Escherichia coli* heat-stable enterotoxin by oligonucleotide-directed mutagenesis," Infection and Immunity, 1987, 55, 2121-2125.
Voller, A., et al., "Immunoassays for the 80's," University Park, 1981.
Sack, "Human diarrheal disease caused by enterotoxigenic *Escherichia coli*," Ann. Rev. Microbial., 1975, 29, 333-353.
Shimonishi, et al., "Mode of disulfide bond formation of a heat-stable entertoxin (.sub.sth)produced by a human strain of enterotoxigenic *Escherichia coli*," Febs. Letts., 1987, 215, 165-170.
So, et al., "Nucleotide sequence of the bacterial transposon Tn1681 encoding a heat-stable (ST) toxin and its identification in enterotoxigenic *Escherichia coli* strains," Proc. Natl. Acad. Sci. USA, 1980, 77, 4011-4015.
Spitler, et al., "Therapy of patients with malignant melanoma using a monoclonal antimelanoma antibody-ricin A chain immunotoxin," Cancer Res., 1987, 47, 1717-1723.
Steinstraber, et al., "Selection of nuclides for immunoscintigraphy Immunotherapy," J. Nucl. Med., 1988, 5, 875.
Thompson, et al., "Biological and immunological characteristics of .sup.125 1-4 Tyr and-18Try *Escherichia coli* heat-stable enterotoxin species purified by high-performance liquid chromatography," Analytical Biochemistry, 1985, 148, 26-36.
Thorpe, et al., "New coupling agents for the synthesis of immunotoxins containing a hindered disulfide bond with improved stability in vivo," Cancer Research, 1987, 47, 5924-5931.
Waldman et al., "Influence of a glycine or proline substitutuion on the functional properties of a 14-amino-acid analog of *Escherichia coli* heat-stable enterotoxin," Infection and Immunity, 1988, 57, 2420-2424.
Wessels, et al., "Radionuclide selection and model absorbed dose calculations for radiolabeled tumor associated antibodies," Med. Phys., 1984, 11, 638-645.
Worrell, et al., "Effect of linkage variation on pharmacokinetics of ricin A chain-antibody conjugates in normal rats," Anti-Cancer Drug Design, 1986, 1, 179-188.
Yoshimura, et al., "Essential structure for full enterotoxigenic activity of heat-stable enterotoxin produced by enterotoxigenic *Escherichia coli*," FEBS, 1985, 2232(181), 138-142.

Barchel, et al., "Radioimaging and Radiiotherapy," New York, 1983.
Hardingham, J.E., et al., "Immunobead-PCR: A technique for the detection of circulating tumor cots using immunomagnetic beads and the polymerase chain reaction,"Cancer Res., 1993, 53, 3455-3458.
Ceriani, R., et al., "Variability in surface antigen expression of human breast epithelial cells cultured from normal breast, normal tissue peripheral to breast carcinomas, and breast carcinomas," Cancer Res., 1984, 44, 3033-3039.
Ceriani, R., et al., "Circulating human mammary epithelial antigens in breast cancer," PNAS USA, 1982, 79, 5420-5424.
Drewett, J., et al., "The family of guanylyl cyclase receptors and their ligands." Endocrine Reviews, 1994, 15(2), 135-162.
Forte, L. et al., "Receptors and cGMP Signalling Mechanism for *E. coli* Enterotoxin in Opossum Kidney", Am J. Physiol. Nov. 1988, 255(5 Pt. 2), F1040-F1046.
Forte, L. et al., "*Escherichia coli* Enterotoxin Receptors: Localization in Opossum Kidney, Intestine, and Testis", Am. J. Physiol. Nov. 1989, 257 (5 Pt. 2), F874-881.
Forte, I. et al., "Guanylin: A Peptide Regulator of Epithelial Transport", FASEB J. 1995, 9, 643 650.
Guerrant, R. et al., "Activation of Intestinal Guanylate Cyclase by Heat-Stable Enterotoxin of *Escherichia coli*: Studies of Tissue Specificity, Potential Receptors,and Intermediates", J. Infect. Dis. Aug. 1980, 142(2), 220-228.
Krause, W. et al., "Autoradiographic Demonstration of Specific Bindings Site for *E. coli* Enterotoxin in Various Epithelia of the North American Opossum", Cell Tissue Res. 1990, 260, 387-394.
Lima, A. et al., "The Effects of *Escherichia coli* Heat-Stable Enterotoxin in Renal Sodium Tubular Transport", Pharmacology & Toxicology 1992, 70, 163-167.
Maderstadt, M. et al., "Antibody Conjugates and Malignant Disease", CRC Press, Boca Raton, 1991, pp. 42-45 and 110-152.
Rao, M. et al., "Mode of Action of Heat-Stable *Escherichia coli* Entertoxin Tissue and Subcellular Specificities and Role of Cyclic GMP", Biochimica et Biophysica Acta 1980, 632, 35-46.
Schulz, S. et al., "Cloning and Expression of Guanylin", The J. Of Biological Chem. 1992, 267(23), 16019-16021.
White, A. et al.,"Opossum Kidney Contains a Functional Receptor for the *Escherichia coli* Heat-Stable Enterotoxin", Biochemical and Biophysical Res. Comm., 1989, 159(1), 363-367.
Bailey's Textbook of Histology, 16th Ed., Coperhaven, et al., Williams and Wilkins, Baltimore, MD, p. 404, 1975.
Bostick, P.J., "Limitations of specific reverse-transcriptase polymerase chain reaction markers in the detection of metastases in the lymph nodes and blood of breast cancer patients," XP-000929382, J. Clinical Oncology, Aug. 1998, 16(8), 2632-2640.
Bustin, S.A., et al., "Detection of cytokeratins 19/20 and guanylyl cyclase C in peripheral blood of colorectal cancer patients," British J. Cancer, XP-000949369, 1999, 79(11/12), 1813-1820.
Champelovier, P., et al., "CK20 gene expression: technical limits for the detection of circulating tumor cells," Anticancer Research, XP-000949390, 1999, 19, 2073-2078.
Wu, G.Y., et al., "Evidence for targeted gene delivery to Hep G2 hepatoma cells in vitro," Biochem., 1988, 27, 887-892.
Eschwege, P., "Haematogenous dissemination of prostatic epithelial cells during radical prostatectomy," Lancet, XP-001145689, Dec. 9, 1995, 346, 1528-1530.
Gala, J-L., et al., "Expression of prostate-specific antigen and prostate-specific membrane antigen transcripts in blood cells: implications for the detection of hematogenous prostate cells and standardization," Clinical Chemistry, XP-002232888,1998, 44(3), 472-481.
Gala, J-L., et al., "Sensitivity or specificity of reverse transcriptase-polymerase chain reaction assays: the real challenge for molecular staging of prostatic carcinomas," Letter to the Editor, Int. J. Cancer, XP-002232687, 1998, 77, 161-163.
Grasso, Y.Z., et al., "Combined nested RT-PCR assay for prostate-specific antigen and prostate-specific membrane antigen in prostate cancer patients: correlation with pathological stage," Cancer Research, XP-001145491, Apr. 1, 1998, 58, 1456-1459.

(56) References Cited

OTHER PUBLICATIONS

Israeli, R.S., et al., "Sensitive nested reverse transcription polymerase chain reaction detection of circulating prostatic tumor cells: comparison of prostate-specific membrane antigen and prostate-specific antigen-based assays," Cancer Research,XP-000931336, Dec. 15, 1994, 54, 6306-6410.

Miltenyi S., et al., "High gradient magnetic cell separation with MACS," Cytometry, XP-000999711, 1990, 11, 231-238.

Neumaier, M., et al., "Diagnosis of micrometastases by the amplification tissue-specific genes" Gene, 1995, 159, 43-47.

Smth, M.R., "Prostatic-specific antigen messenger RNA is expressed in non-prostate cells: implications for detection of micrometastases," Cancer Research, XP002910142, Jun. 15, 1995, 55, 2640-2644.

Wadman S.Ca., et al., "Heterogeneity of guanylyl cyclase C expressed by human colorectal cancer cell lines in vitro." Cancer Epidemiology, Biomarkers & Prevention, XP009006094, Jun. 1998, 7, 505-514.

Wong, I.H.N., et al., "Quantitative analysis of circulating tumour cells in breast cancer patients using reverse. transcriptae polymerase chain reaction," European J. of Cancer, XP00438226, Sep. 1999, p. S90 (abstract).

Iannettoni, M.D. et al., "Detection of Barrett's adenocarcinoma of the gastric cardia with sucrase isomaltase and p53", Ann. Thorac. Surg., 1996, 62, 1460-1466.

* cited by examiner

```
                             SEQUENCE LISTING

<160> NUMBER OF SEQ ID NOS: 56

<210> SEQ ID NO 1
<211> LENGTH: 3787
<212> TYPE: DNA
<213> ORGANISM: Homo sapiens

<400> SEQUENCE: 1
tggagtgggc tgagggactc cactagaggc tgtccatctg gattccctgc ctccctagga      60
gcccaacaga gcaaagcaag tgggcacaag gagtatggtt ctaacgtgat tggggtcatg     120
aagacgttgc tgttggactt ggctttgtgg tcactgctct tccagcccgg gtggctgtcc     180
tttagttccc aggtgagtca gaactgccac aatggcagct atgaaatcag cgtcctgatg     240
atgggcaact cagcctttgc agagccctg aaaaacttgg aagatgcggt gaatgagggg     300
ctggaaatag tgagaggacg tctgcaaaat gctggcctaa atgtgactgt gaacgctact     360
ttcatgtatt cggatggtct gattcataac tcaggcgact gccggagtag cacctgtgaa     420
ggcctcgacc tactcaggaa aatttcaaat gcacaacgga tgggctgtgt cctcataggg     480
ccctcatgta catactccac cttccagatg taccttgaca cagaattgag ctacccatg     540 atctcagctg aagttttgg attgtcatgt gactataaag aaaccttaac caggctgatg     600
tctccagcta gaaagttgat gtacttcttg gttaactttt ggaaaaccaa cgatctgccc     660
ttcaaaactt attcctggag cacttcgtat gtttacaaga atggtacaga aactgaggac     720
tgtttctggt accttaatgc tctggaggct agcgtttcct atttctccca cgaactcggc     780
tttaaggtgg tgttaagaca agataaggag tttcaggata tcttaatgga ccacaacagg     840
aaaagcaatg tgattattat gtgtggtggt ccagagttcc tctacaagct gaagggtgac     900
cgagcagtgg ctgaagacat tgtcattatt ctagtggatc tttcaatga ccagtacttg     960 gaggacaatg tcacagcccc tgactatatg aaaaatgtcc ttgttctgac gctgtctcct    1020
gggaattccc ttctaaatag ctctttctcc aggaatctat caccaacaaa acgagacttt    1080
cgtcttgcct atttgaatgg aatcctcgtc tttggacata tgctgaagat atttcttgaa    1140
aatggagaaa atattaccac ccccaaattt gctcatgcct tcaggaatct cacttttgaa    1200
gggtatgacg gtccagtgac cttggatgac tggggggatg ttgacagtac catggtgctt    1260
```

```
ctgtatacct ctgtggacac caagaaatac aaggttcttt tgacctatga tacccacgta   1320
aataagacct atcctgtgga tatgagcccc acattcactt ggaagaactc taaacttcct   1380
aatgatatta caggccgggg ccctcagatc ctgatgattg cagtcttcac cctcactgga   1440
gctgtggtgc tgctcctgct cgtcgctctc ctgatgctca gaaaatatag aaagagattat  1500
gaacttcgtc agaaaaaatg gtcccacatt cctcctgaaa atatctttcc tctggagacc   1560
aatgagacca atcatgttag cctcaagatc gatgatgaca aaagacgaga tacaatccag   1620
agactacgac agtgcaaata cgtcaaaaag cgagtgattc tcaaagatct caagcacaat   1680
gatggtaatt tcactgaaaa acagaagata gaattgaaca agttgcttca gattgactat   1740
tacaccctaa ccaagttcta cgggacagtg aaactggata ccatgatctt cggggtgata   1800
gaatactgtg agagaggatc cctccgggaa gttttaaatg cacaatttc ctaccctgat    1860
ggcacattca tggattggga gtttaagatc tctgtcttgt atgacattgc taagggaatg   1920
tcatatctgc actccagtaa gacagaagtc catggtcgtc tgaaatctac caactgcgta   1980
gtggacagta gaatggtggt gaagatcact gattttggct gcaattccat tttgcctcca   2040
aaaaaggacc tgtggacagc tccagagcac ctccgccaag ccaacatctc tcagaaagga  2100
gatgtgtaca gctatgggat catcgcacag gagatcattg cggaaaga aaccttctac     2160
actttgagct gtcgggaccg gaatgagaag attttcagag tggaaaattc caatggaatg   2220
aaacccttcc gcccagattt attcttggaa acagcagagg aaaaagagct agaagtgtac   2280
ctacttgtaa aaactgttg ggaggaagat ccagaaaaga gaccagattt caaaaaaatt    2340
gagactacac ttgccaagat atttggactt tttcatgacc aaaaaaatga agctatatg    2400
gataccttga tccgacgtct acagctatat tctcgaaacc tggaacatct ggtagaggaa   2460
aggacacagc tgtacaaggc agagagggac agggctgaca gacttaactt tatgttgctt   2520
ccaaggctag tggtaaagtc tctgaaggag aaaggctttg tggagccgga actatatgag   2580
gaagttacaa tctacttcag tgacattgta ggtttcacta ctatctgcaa atacagcacc   2640
cccatggaag tggtggacat gcttaatgac atctataaga gttttgacca cattgttgat   2700
catcatgatg tctacaaggt ggaaaccatc ggtgatgcgt acatggtggc tagtggtttg   2760
cctaagagaa atggcaatcg gcatgcaata gacattgcca agatggcctt ggaaatcctc   2820
agcttcatgg ggacctttga gctggagcat cttcctggcc tcccaatatg gattcgcatt   2880
ggagttcact ctggtccctg tgctgctgga gttgtgggaa tcaagatgcc tcgttattgt   2940
ctatttggag atacggtcaa cacagcctct aggatggaat ccactggcct cccttttgaga  3000
attcacgtga gtggctccac catagccatc ctgaagagaa ctgagtgcca gttcctttat   3060
gaagtgagag agaaacata cttaaaggga agaggaaatg agactaccta ctggctgact   3120
gggatgaagg accagaaatt caacctgcca accctccta ctgtggagaa tcaacagcgt   3180
ttgcaagcag aattttcaga catgattgcc aactcttac agaaaagaca ggcagcaggg   3240
ataagaagcc aaaaacccag acgggtagcc agctataaaa aaggcactct ggaatacttg   3300
cagctgaata ccacagacaa ggagagcacc tatttttaaa cctaaatgag gtataaggac   3360
tcacacaaat taaatacag ctgcactgag gccaggcacc ctcaggtgtc ctgaaagctt    3420
actttcctga gacctcatga ggcagaaatg tcttaggctt ggctgccctg tttggaccat   3480
ggactttctt tgcatgaatc agatgtgttc tcagtgaaat aactaccttc cactctggaa   3540
ccttattcca gcagttgttc cagggagctt ctacctggaa agaaaagaa tttcattat    3600
tttttgtttg tttatttta tcgtttttgt ttactggctt tccttctgta ttcataagat    3660
```

-continued

```
ttttttaaatt gtcataatta tattttaaat acccatcttc attaaagtat atttaactca    3720
taatttttgc agaaaatatg ctatatatta ggcaagaata aaagctaaag gtttcccaaa    3780
aaaaaaa                                                              3787
```

<210> SEQ ID NO 2
<211> LENGTH: 1073
<212> TYPE: PRT
<213> ORGANISM: Homo sapiens

<400> SEQUENCE: 2

```
Met Lys Thr Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
                20                  25                  30

Gly Ser Tyr Glu Ile Ser Val Leu Met Met Gly Asn Ser Ala Phe Ala
                35                  40                  45

Glu Pro Leu Lys Asn Leu Glu Asp Ala Val Asn Glu Gly Leu Glu Ile
                50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                    85                  90                  95

Ser Ser Thr Cys Glu Gly Leu Asp Leu Leu Arg Lys Ile Ser Asn Ala
                    100                 105                 110

Gln Arg Met Gly Cys Val Leu Ile Gly Pro Ser Cys Thr Tyr Ser Thr
                    115                 120                 125

Phe Gln Met Tyr Leu Asp Thr Glu Leu Ser Tyr Pro Met Ile Ser Ala
        130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                    165                 170                 175

Thr Asn Asp Leu Pro Phe Lys Thr Tyr Ser Trp Ser Thr Ser Tyr Val
                    180                 185                 190

Tyr Lys Asn Gly Thr Glu Thr Glu Asp Cys Phe Trp Tyr Leu Asn Ala
                    195                 200                 205

Leu Glu Ala Ser Val Ser Tyr Phe Ser His Glu Leu Gly Phe Lys Val
        210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                    245                 250                 255

Lys Leu Lys Gly Asp Arg Ala Val Ala Glu Asp Ile Val Ile Ile Leu
                    260                 265                 270

Val Asp Leu Phe Asn Asp Gln Tyr Leu Glu Asp Asn Val Thr Ala Pro
                    275                 280                 285

Asp Tyr Met Lys Asn Val Leu Val Leu Thr Leu Ser Pro Gly Asn Ser
        290                 295                 300

Leu Leu Asn Ser Ser Phe Ser Arg Asn Leu Ser Pro Thr Lys Arg Asp
305                 310                 315                 320

Phe Arg Leu Ala Tyr Leu Asn Gly Ile Leu Val Phe Gly His Met Leu
                    325                 330                 335

Lys Ile Phe Leu Glu Asn Gly Glu Asn Ile Thr Thr Pro Lys Phe Ala
                    340                 345                 350
```

```
His Ala Phe Arg Asn Leu Thr Phe Glu Gly Tyr Asp Gly Pro Val Thr
            355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro Gln Ile Leu
            420                 425                 430

Met Ile Ala Val Phe Thr Leu Thr Gly Ala Val Val Leu Leu Leu Leu
            435                 440                 445

Val Ala Leu Leu Met Leu Arg Lys Tyr Arg Lys Asp Tyr Glu Leu Arg
    450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Asp Lys Arg
                485                 490                 495

Arg Asp Thr Ile Gln Arg Leu Arg Gln Cys Lys Tyr Val Lys Lys Arg
            500                 505                 510

Val Ile Leu Lys Asp Leu Lys His Asn Asp Gly Asn Phe Thr Glu Lys
    515                 520                 525

Gln Lys Ile Glu Leu Asn Lys Leu Leu Gln Ile Asp Tyr Tyr Thr Leu
            530                 535                 540

Thr Lys Phe Tyr Gly Thr Val Lys Leu Asp Thr Met Ile Phe Gly Val
545                 550                 555                 560

Ile Glu Tyr Cys Glu Arg Gly Ser Leu Arg Glu Val Leu Asn Asp Thr
                565                 570                 575

Ile Ser Tyr Pro Asp Gly Thr Phe Met Asp Trp Glu Phe Lys Ile Ser
            580                 585                 590

Val Leu Tyr Asp Ile Ala Lys Gly Met Ser Tyr Leu His Ser Ser Lys
    595                 600                 605

Thr Glu Val His Gly Arg Leu Lys Ser Thr Asn Cys Val Val Asp Ser
610                 615                 620

Arg Met Val Val Lys Ile Thr Asp Phe Gly Cys Asn Ser Ile Leu Pro
625                 630                 635                 640

Pro Lys Lys Asp Leu Trp Thr Ala Pro Glu His Leu Arg Gln Ala Asn
                645                 650                 655

Ile Ser Gln Lys Gly Asp Val Tyr Ser Tyr Gly Ile Ile Ala Gln Glu
            660                 665                 670

Ile Ile Leu Arg Lys Glu Thr Phe Tyr Thr Leu Ser Cys Arg Asp Arg
    675                 680                 685

Asn Glu Lys Ile Phe Arg Val Glu Asn Ser Asn Gly Met Lys Pro Phe
690                 695                 700

Arg Pro Asp Leu Phe Leu Glu Thr Ala Glu Glu Lys Glu Leu Glu Val
705                 710                 715                 720

Tyr Leu Leu Val Lys Asn Cys Trp Glu Glu Asp Pro Glu Lys Arg Pro
                725                 730                 735

Asp Phe Lys Lys Ile Glu Thr Thr Leu Ala Lys Ile Phe Gly Leu Phe
            740                 745                 750

His Asp Gln Lys Asn Glu Ser Tyr Met Asp Thr Leu Ile Arg Arg Leu
    755                 760                 765

Gln Leu Tyr Ser Arg Asn Leu Glu His Leu Val Glu Glu Arg Thr Gln
```

```
Leu Tyr Lys Ala Glu Arg Asp Arg Ala Asp Arg Leu Asn Phe Met Leu
785                 790                 795                 800

Leu Pro Arg Leu Val Val Lys Ser Leu Lys Glu Lys Gly Phe Val Glu
                805                 810                 815

Pro Glu Leu Tyr Glu Val Thr Ile Tyr Phe Ser Asp Ile Val Gly
                820                 825                 830

Phe Thr Thr Ile Cys Lys Tyr Ser Thr Pro Met Glu Val Val Asp Met
                835                 840                 845

Leu Asn Asp Ile Tyr Lys Ser Phe Asp His Ile Val Asp His His Asp
                850                 855                 860

Val Tyr Lys Val Glu Thr Ile Gly Asp Ala Tyr Met Val Ala Ser Gly
865                 870                 875                 880

Leu Pro Lys Arg Asn Gly Asn Arg His Ala Ile Asp Ile Ala Lys Met
                885                 890                 895

Ala Leu Glu Ile Leu Ser Phe Met Gly Thr Phe Glu Leu Glu His Leu
                900                 905                 910

Pro Gly Leu Pro Ile Trp Ile Arg Ile Gly Val His Ser Gly Pro Cys
                915                 920                 925

Ala Ala Gly Val Val Gly Ile Lys Met Pro Arg Tyr Cys Leu Phe Gly
930                 935                 940

Asp Thr Val Asn Thr Ala Ser Arg Met Glu Ser Thr Gly Leu Pro Leu
945                 950                 955                 960

Arg Ile His Val Ser Gly Ser Thr Ile Ala Ile Leu Lys Arg Thr Glu
                965                 970                 975

Cys Gln Phe Leu Tyr Glu Val Arg Gly Glu Thr Tyr Leu Lys Gly Arg
                980                 985                 990

Gly Asn Glu Thr Thr Tyr Trp Leu Thr Gly Met Lys Asp Gln Lys Phe
                995                 1000                1005

Asn Leu Pro Thr Pro Pro Thr Val Glu Asn Gln Gln Arg Leu Gln
    1010                1015                1020

Ala Glu Phe Ser Asp Met Ile Ala Asn Ser Leu Gln Lys Arg Gln
    1025                1030                1035

Ala Ala Gly Ile Arg Ser Gln Lys Pro Arg Arg Val Ala Ser Tyr
    1040                1045                1050

Lys Lys Gly Thr Leu Glu Tyr Leu Gln Leu Asn Thr Thr Asp Lys
    1055                1060                1065

Glu Ser Thr Tyr Phe
    1070

<210> SEQ ID NO 3
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 3

Asn Thr Phe Tyr Cys Cys Glu Leu Cys Cys Tyr Pro Ala Cys Ala Gly
1               5                   10                  15

Cys Asn

<210> SEQ ID NO 4
<211> LENGTH: 19
<212> TYPE: PRT
<213> ORGANISM: Artificial Sequence
```

```
<220> FEATURE:
<223> OTHER INFORMATION: Synthetic Sequence

<400> SEQUENCE: 4

Asn Asn Thr Phe Tyr Cys Cys Glu Leu Cys Cys Asn Pro Ala Cys Ala
1               5                   10                  15

Gly Cys Tyr

<210> SEQ ID NO 5
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 5

Asn Ser Ser Asn Tyr Cys Cys Glu Leu Cys Cys Asn Pro Ala Cys Asn
1               5                   10                  15

Gly Cys Tyr

<210> SEQ ID NO 6
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 6

Pro Asn Thr Cys Glu Ile Cys Ala Tyr Ala Ala Cys Thr Gly Cys
1               5                   10                  15

<210> SEQ ID NO 7
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 7

Asn Asn Thr Phe Tyr Cys Cys Glu Leu Cys Cys Asn Pro Ala Cys Ala
1               5                   10                  15

Gly Cys

<210> SEQ ID NO 8
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 8

Asn Thr Phe Tyr Cys Cys Glu Leu Cys Cys Asn Pro Ala Cys Ala Gly
1               5                   10                  15

Cys

<210> SEQ ID NO 9
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 9

Thr Phe Tyr Cys Cys Glu Leu Cys Cys Asn Pro Ala Cys Ala Gly Cys
```

```
<210> SEQ ID NO 10
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 10

Phe Tyr Cys Cys Glu Leu Cys Cys Asn Pro Ala Cys Ala Gly Cys
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 11

Tyr Cys Cys Glu Leu Cys Cys Asn Pro Ala Cys Ala Gly Cys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 12

Cys Cys Glu Leu Cys Cys Asn Pro Ala Cys Ala Gly Cys
1               5                   10

<210> SEQ ID NO 13
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 13

Asn Thr Phe Tyr Cys Cys Glu Leu Cys Cys Asn Pro Ala Cys Ala Gly
1               5                   10                  15

Cys Tyr

<210> SEQ ID NO 14
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 14

Thr Phe Tyr Cys Cys Glu Leu Cys Cys Asn Pro Ala Cys Ala Gly Cys
1               5                   10                  15

Tyr

<210> SEQ ID NO 15
<211> LENGTH: 16
<212> TYPE: PRT
<213> ORGANISM: Artificial Sequence
<220> FEATURE:
<223> OTHER INFORMATION: Synthetic Sequence
```

<400> SEQUENCE: 15

Phe Tyr Cys Cys Glu Leu Cys Cys Asn Pro Ala Cys Ala Gly Cys Tyr
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 16

Tyr Cys Cys Glu Leu Cys Cys Asn Pro Ala Cys Ala Gly Cys Tyr
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 17

Cys Cys Glu Leu Cys Cys Asn Pro Ala Cys Ala Gly Cys Tyr
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 18

Asn Thr Phe Tyr Cys Cys Glu Leu Cys Cys Tyr Pro Ala Cys Ala Gly
1               5                   10                  15

Cys

<210> SEQ ID NO 19
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 19

Thr Phe Tyr Cys Cys Glu Leu Cys Cys Tyr Pro Ala Cys Ala Gly Cys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 20

Phe Tyr Cys Cys Glu Leu Cys Cys Tyr Pro Ala Cys Ala Gly Cys
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 21

Tyr Cys Cys Glu Leu Cys Cys Tyr Pro Ala Cys Ala Gly Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 22

Cys Cys Glu Leu Cys Cys Tyr Pro Ala Cys Ala Gly Cys
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 23

Thr Phe Tyr Cys Cys Glu Leu Cys Cys Tyr Pro Ala Cys Ala Gly Cys
1               5                   10                  15

Asn

<210> SEQ ID NO 24
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 24

Phe Tyr Cys Cys Glu Leu Cys Cys Tyr Pro Ala Cys Ala Gly Cys Asn
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 25

Tyr Cys Cys Glu Leu Cys Cys Tyr Pro Ala Cys Ala Gly Cys Asn
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 26

Cys Cys Glu Leu Cys Cys Tyr Pro Ala Cys Ala Gly Cys Asn
1               5                   10

<210> SEQ ID NO 27
<211> LENGTH: 18
<212> TYPE: PRT
<213> ORGANISM: Artificial Sequence
<220> FEATURE:

<223> OTHER INFORMATION: Synthetic Sequence

<400> SEQUENCE: 27

Asn Ser Ser Asn Tyr Cys Cys Glu Leu Cys Cys Asn Pro Ala Cys Thr
1               5                   10                  15
Gly Cys

<210> SEQ ID NO 28
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 28

Ser Ser Asn Tyr Cys Cys Glu Leu Cys Cys Asn Pro Ala Cys Thr Gly
1               5                   10                  15
Cys

<210> SEQ ID NO 29
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 29

Ser Asn Tyr Cys Cys Glu Leu Cys Cys Asn Pro Ala Cys Thr Gly Cys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 30

Asn Tyr Cys Cys Glu Leu Cys Cys Asn Pro Ala Cys Thr Gly Cys
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 31

Tyr Cys Cys Glu Leu Cys Cys Asn Pro Ala Cys Thr Gly Cys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 32

Cys Cys Glu Leu Cys Cys Asn Pro Ala Cys Thr Gly Cys
1               5                   10

<210> SEQ ID NO 33
<211> LENGTH: 18

```
<212> TYPE: PRT
<213> ORGANISM: Artificial Sequence
<220> FEATURE:
<223> OTHER INFORMATION: Synthetic Sequence

<400> SEQUENCE: 33

Ser Ser Asn Tyr Cys Cys Glu Leu Cys Cys Asn Pro Ala Cys Thr Gly
1               5                   10                  15

Cys Tyr

<210> SEQ ID NO 34
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 34

Ser Asn Tyr Cys Cys Glu Leu Cys Cys Asn Pro Ala Cys Thr Gly Cys
1               5                   10                  15

Tyr

<210> SEQ ID NO 35
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 35

Asn Tyr Cys Cys Glu Leu Cys Cys Asn Pro Ala Cys Thr Gly Cys Tyr
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 36

Tyr Cys Cys Glu Leu Cys Cys Asn Pro Ala Cys Thr Gly Cys Tyr
1               5                   10                  15

<210> SEQ ID NO 37
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 37

Cys Cys Glu Leu Cys Cys Asn Pro Ala Cys Thr Gly Cys Tyr
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 38

Asn Thr Phe Tyr Cys Cys Glu Leu Cys Cys Asn Pro Ala Cys Ala Gly
1               5                   10                  15
```

Cys Tyr

<210> SEQ ID NO 39
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 39

Asn Thr Phe Tyr Cys Cys Glu Leu Cys Cys Ala Pro Ala Cys Ala Gly
1               5                   10                  15

Cys Tyr

<210> SEQ ID NO 40
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 40

Asn Thr Phe Tyr Cys Cys Glu Leu Cys Cys Asn Ala Ala Cys Ala Gly
1               5                   10                  15

Cys Tyr

<210> SEQ ID NO 41
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 41

Asn Thr Phe Tyr Cys Cys Glu Leu Cys Cys Asn Pro Ala Cys Ala Gly
1               5                   10                  15

Cys

<210> SEQ ID NO 42
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 42

Tyr Cys Cys Glu Leu Cys Cys Asn Pro Ala Cys Ala Gly Cys Tyr
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 43

Tyr Cys Cys Glu Leu Cys Cys Asn Pro Ala Cys Ala Gly Cys
1               5                   10

<210> SEQ ID NO 44
<211> LENGTH: 14
<212> TYPE: PRT
<213> ORGANISM: Artificial Sequence
<220> FEATURE:

<223> OTHER INFORMATION: Synthetic Sequence

<400> SEQUENCE: 44

Cys Cys Glu Leu Cys Cys Asn Pro Ala Cys Ala Gly Cys Tyr
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 45

Cys Cys Glu Leu Cys Cys Asn Pro Ala Cys Ala Gly Cys
1               5                   10

<210> SEQ ID NO 46
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 46

Gln Ala Cys Asp Pro Pro Ser Pro Pro Ala Glu Val Cys Cys Asp Val
1               5                   10                  15

Cys Cys Asn Pro Ala Cys Ala Gly Cys
            20                  25

<210> SEQ ID NO 47
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 47

Ile Asp Cys Cys Ile Cys Asn Pro Ala Cys Phe Gly Cys Leu Asn
1               5                   10                  15

<210> SEQ ID NO 48
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 48

Ser Ser Asp Trp Asp Cys Cys Asp Val Cys Cys Asn Pro Ala Cys Ala
1               5                   10                  15

Gly Cys

<210> SEQ ID NO 49
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 49

Asn Ser Ser Asn Tyr Cys Cys Glu Leu Cys Cys Tyr Pro Ala Cys Thr
1               5                   10                  15

Gly Cys Tyr

<210> SEQ ID NO 50
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 50

Cys Cys Asp Val Cys Cys Asn Pro Ala Cys Thr Gly Cys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 51

Cys Cys Asp Val Cys Cys Tyr Pro Ala Cys Thr Gly Cys Tyr
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 52

Cys Cys Asp Leu Cys Cys Asn Pro Ala Cys Ala Gly Cys Tyr
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 53

Cys Cys Gln Leu Cys Cys Asn Pro Ala Cys Thr Gly Cys Tyr
1               5                   10

<210> SEQ ID NO 54
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 54

Cys Cys Gln Leu Cys Cys Asn Pro Ala Cys Thr Gly Cys Tyr Pro Gly
1               5                   10                  15

Thr Cys Glu Ile Cys Ala Tyr Ala Ala Cys Thr Gly Cys
            20                  25

<210> SEQ ID NO 55
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 55

Gln Glu Asp Cys Glu Leu Cys Ile Asn Val Ala Cys Thr Gly Cys

```
                    1               5              10              15

<210> SEQ ID NO 56
<211> LENGTH: 16
<212> TYPE: PRT
<213> ORGANISM: Artificial Sequence
<220> FEATURE:
<223> OTHER INFORMATION: Peptide

<400> SEQUENCE: 56

Asn Asp Asp Cys Glu Leu Cys Val Asn Val Ala Cys Thr Gly Cys Leu
1               5                  10                  15
```

COMPOSITIONS AND METHODS FOR IDENTIFYING AND TARGETING CANCER CELLS OF ALIMENTARY CANAL ORIGIN

CROSS REFERENCE TO RELATED PATENT APPLICATIONS

This application claims priority to U.S. Provisional Application No. 60/192,229 filed Mar. 27, 2000, which is incorporated herein by reference.

This application is also related to U.S. Pat. No. 5,518,888, issued May 21, 1996, U.S. Pat. No. 5,601,990 issued Feb. 11, 1997, U.S. Pat. No. 6,060,037 issued Apr. 26, 2000, U.S. Pat. No. 5,962,220 issued Oct. 5, 1999, and U.S. Pat. No. 5,879,656 issued Mar. 9, 1999, which are each incorporated herein by reference and U.S. patent application Ser. No. 09/180,237 filed Mar. 12, 1997, which is incorporated herein by reference.

FIELD OF THE INVENTION

The present invention relates to in vitro diagnostic methods for detecting cancer cells of the alimentary canal, particularly primary and metastatic stomach and esophageal cancer, and to kits and reagents for performing such methods. The present invention relates to compounds and methods for in vivo imaging and treatment of tumors originating from the alimentary canal, particularly primary and metastatic stomach and esophageal tumors. The present invention relates to methods and compositions for making and using targeted gene therapy, antisense and drug compositions. The present invention relates to prophylactic and therapeutic vaccines against cancer cells of the alimentary canal, particularly primary and metastatic stomach and esophageal cancer and compositions and methods of making and using the same.

BACKGROUND OF THE INVENTION

There is a need for reagents, kits and methods for screening, diagnosing and monitoring individuals with cancer originating from the alimentary canal, particularly primary and metastatic stomach and esophageal cancer. There is a need for reagents, kits and methods for identifying and confirming that a cancer of unknown origin is originating from the alimentary canal and for analyzing tissue and cancer samples to identify and confirm cancer originating from the alimentary canal and to determine the level of migration of such cancer cells. There is a need for compositions which can specifically target stomach and esophageal cancer cells. There is a need for imaging agents which can specifically bind to stomach and esophageal cancer cells. There is a need for improved methods of imaging stomach and esophageal cancer cells. There is a need for therapeutic agents which can specifically bind to stomach and esophageal cancer cells. There is a need for improved methods of treating individuals who are suspected of suffering from primary and/or metastatic stomach or esophageal cancer. There is a need for vaccine composition to treat stomach and esophageal cancer. There is a need for vaccine composition to treat and prevent stomach and esophageal cancer. There is a need for therapeutic agents which can specifically deliver gene therapeutics, antisense compounds and other drugs to stomach and esophageal cancer cells.

SUMMARY OF THE INVENTION

The invention further relates to in vitro methods of determining whether or not an individual has cancer originating from the alimentary canal, particularly primary and metastatic stomach and esophageal cancer. The present invention relates to in vitro methods of examining samples of non-colorectal tissue and body fluids from an individual to determine whether or not GCC, which is expressed by normal colon cells and by colorectal, stomach and esophageal tumor cells, is being expressed by cells in samples other than colon. The presence of GCC protein or of the GCC gene transcript in samples outside the colorectal track is indicative of expression of GCC and is evidence that the individual may be suffering from metastasized colon cancer or primary or metastatic stomach and/or esophageal cancer. In patients suspected of suffering from colorectal cancer, the presence of GCC protein or of the GCC gene transcript in samples outside the colorectal track is supportive of the conclusion that the individual is suffering from metastatic colorectal cancer. The diagnosis of metastatic colorectal cancer may be made or confirmed. In patients suspected of suffering from stomach or esophageal cancer, the presence of GCC protein or of the GCC gene transcript in samples outside the colorectal track is supportive of the conclusion that the individual is suffering from primary and/or metastatic stomach or esophageal cancer. The diagnosis of primary and/or metastatic stomach or esophageal cancer may be made or confirmed.

The invention further relates to in vitro methods of determining whether or not tumor cells suspected of being stomach or esophageal cancer are stomach or esophageal in origin. The present invention relates to in vitro methods of diagnosing whether or not an individual suspected of suffering from stomach or esophageal cancer is suffering from stomach or esophageal cancer. The present invention relates to in vitro methods of examining samples of tumors from an individual to determine whether or not GCC protein, which is expressed by colorectal, stomach or esophageal tumor cells, is being expressed by the tumor cells. The presence of a GCC protein or of the GCC gene transcript in a sample from a patient suspected of having stomach or esophageal cancer is indicative of expression of GCC and evidence that the individual may be suffering from stomach or esophageal cancer. In tumors which are suspected of being stomach or esophageal tumors, the presence of a GCC protein or of the GCC gene transcript supports the conclusion that the tumors are of stomach or esophageal cancer and the diagnosis of stomach or esophageal cancer.

The invention further relates to in vitro kits for practicing the methods of the invention and to reagents and compositions useful as components in such in vitro kits of the invention.

The invention further relates to a method of imaging primary and metastatic stomach and esophageal tumors and to methods of treating an individual suspected of suffering from primary and metastatic stomach and esophageal tumors comprising the steps of administering to said individual a pharmaceutical compositions according to the invention, wherein the compositions or conjugated compounds are present in an amount effective for therapeutic or diagnostic use in humans suffering from primary and/or metastatic stomach or esophageal tumors.

The invention further relates to a method of delivering an active agent to primary and metastatic stomach and esophageal tumor cells comprising the steps of administering to an individual who has primary and/or metastatic stomach or esophageal tumors, a pharmaceutical composition comprising a pharmaceutically acceptable carrier or diluent, and an unconjugated compositions that comprises a liposome that includes GCC ligands on its surface and an active component encapsulated therein.

The invention further relates to killed or inactivated stomach or esophageal tumor cells that comprise a protein comprising at least one epitope of a GCC protein; and to vaccines comprising the same. In some embodiments, the killed or inactivated cells or particles comprise a GCC protein. In some embodiments, the killed or inactivated cells or particles are haptenized.

The invention further relates to methods of treating individuals suffering from stomach or esophageal cancer and to methods of treating individuals susceptible stomach or esophageal cancer. The method of the present invention provides administering to such individuals an effective amount of such vaccines. The invention further relates to the use of such vaccines as immunotherapeutics.

DESCRIPTION OF PREFERRED EMBODIMENTS

Definitions

As used herein, the term "GCC" is meant to refer to the cellular protein guanylin cyclase C (also referred to as ST receptor), which is expressed by normal colorectal cells, as well as primary and metastasized colorectal, stomach and esophageal cancer cells. In normal individuals, GCC is found exclusively in cells of intestine, in particular id cells in the duodenum, small intestine (jejunum and ileum), the large intestine, colon (cecum, ascending colon, transverse colon, descending colon and sigmoid colon) and rectum.

As used herein, the term "functional fragment" as used in the term "functional fragment of a GCC gene transcript" is meant to refer to fragments of GCC gene transcript which are functional with respect to nucleic acid molecules with full length sequences. For example, a functional fragment may be useful as an oligonucleotide or nucleic acid probe, a primer, an antisense oligonucleotide or nucleic acid molecule or a coding sequence. The nucleotide sequence encoding human GCC protein is disclosed in F. J. Sauvage et al. 1991 *J. Biol. Chem.* 266:17912-17918, each of which is incorporated herein by reference.

As used herein, the term "functional fragment" as used in the term "functional fragment of a GCC protein" is meant to fragments of GCC protein which function in the same manner as GCC protein with full length sequences. For example, an immunogenically functional fragment of a GCC protein comprises an epitope recognized by an anti-GCC antibody. A ligand-binding functional fragment of GCC comprises a sequence which forms a structure that can bind to a ligand which recognizes and binds to GCC protein.

As used herein, the term "epitope recognized by an anti-GCC protein antibody" refers to those epitopes specifically recognized by an anti-GCC protein antibody.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies.

As used herein, the term "GCC ligand" is meant to refer to compounds which specifically bind to a GCC protein. Antibodies that bind to GCC are GCC ligands. A GCC ligand may be a protein, peptide or a non-peptide.

As used herein, the term "active agent" is meant to refer to compounds that are therapeutic agents or imaging agents.

As used herein, the term "radiostable" is meant to refer to compounds which do not undergo radioactive decay; i.e. compounds which are not radioactive.

As used herein, the term "therapeutic agent" is meant to refer to chemotherapeutics, toxins, radiotherapeutics, targeting agents or radiosensitizing agents.

As used herein, the term "chemotherapeutic" is meant to refer to compounds that, when contacted with and/or incorporated into a cell, produce an effect on the cell including causing the death of the cell, inhibiting cell division or inducing differentiation.

As used herein, the term "toxin" is meant to refer to compounds that, when contacted with and/or incorporated into a cell, produce the death of the cell.

As used herein, the term "radiotherapeutic" is meant to refer to radionuclides which when contacted with and/or incorporated into a cell, produce the death of the cell.

As used herein, the term "targeting agent" is meant to refer compounds which can be bound by and or react with other compounds. Targeting agents may be used to deliver chemotherapoutics, toxins, enzymes, radiotherapeutics, antibodies or imaging agents to cells that have targeting agents associated with them and/or to convert or otherwise transform or enhance co-administered active agents. A targeting agent may include a moiety that constitutes a first agent that is localized to the cell which when contacted with a second agent either is converted to a third agent which has a desired activity or causes the conversion of the second agent into an agent with a desired activity. The result is the localized agent facilitates exposure of an agent with a desired activity to the cancer cell.

As used herein, the term "radiosensitizing agent" is meant to refer to agents which increase the susceptibility of cells to the damaging effects of ionizing radiation. A radiosensitizing agent permits lower doses of radiation to be administered and still provide a therapeutically effective dose.

As used herein, the term "imaging agent" is meant to refer to compounds which can be detected.

As used herein, the term "GCC binding moiety" is meant to refer to the portion of a conjugated compound that constitutes an GCC ligand.

As used herein, the term "active moiety" is meant to refer to the portion of a conjugated compound that constitutes an active agent.

As used herein, the terms "cojugated compound" and "conjugated composition" are used interchangeably and meant to refer to a compound which comprises a GCC binding moiety and an active moiety and which is capable of binding to GCC. Conjugated compounds according to the present invention comprise a portion which constitutes an GCC ligand and a portion which constitutes an active agent. Thus, conjugated compounds according to the present invention are capable of specifically binding to the GCC and include a portion which is a therapeutic agent or imaging agent. Conjugated compositions may comprise crosslinkers and/or molecules that serve as spacers between the moieties.

As used herein, the terms "crosslinker". "crosslinking agent", "conjugating agent". "coupling agent", "condensation reagent" and "bifunctional crosslinker" are used interchangeably and are meant to refer to molecular groups which are used to attach the GCC ligand and the active agent to thus form the conjugated compound.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain GCC.

As used herein, the term "stomach cancer" is meant to include the well-accepted medical definition that defines stomach cancer as a medical condition characterized by cancer of cells of the stomach.

As used herein, the term "esophageal cancer" is meant to include the well-accepted medical definition that defines esophageal cancer as a medical condition characterized by cancer of cells of the esophagus.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body.

As used herein, the term "metastasized colorectal cancer cells" is meant to refer to colorectal cancer cells which have metastasized. Metastasized colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, the term "metastasized stomach cancer cells" is meant to refer to stomach cancer cells which have metastasized. Metastasized stomach cancer cells localized in a part of the body other than the stomach.

As used herein, the term "metastasized esophageal cancer cells" is is meant to refer to colorectal cancer cells which have metastasized. Metastasized esophageal cancer cells localized in a part of the body other than the esophagus.

As used herein, the term "non-colorectal sample" and "extra-intestinal sample" are used interchangeably and meant to refer to a sample of tissue or body fluid from a source other than colorectal tissue. In some preferred embodiments, the non-colorectal sample is a sample of tissue such as lymph nodes. In some preferred embodiments, the non-colorectal sample is a sample of extra-intestinal tissue which is an adenocarcinoma of unconfirmed origin. In some preferred embodiments, the non-colorectal sample is a blood sample.

As used herein, "an individual suffering from an adenocarcinoma of unconfirmed origin" is meant to refer to an individual who has a tumor in which the origin has not been definitively identified.

As used herein, "an individual is suspected of being susceptible to stomach or esophageal cancer" is meant to refer to an individual who is at a particular risk of developing stomach or esophageal cancer. Examples of individuals at a particular risk of developing stomach or esophageal cancer are those whose family medical history indicates above average incidence of stomach or esophageal cancer among family members and/or those who have already developed stomach or esophageal cancer and have been effectively treated who therefore face a risk of relapse and recurrence.

As used herein, the term "antisense composition" and "antisense molecules" are used interchangeably and are meant to refer to compounds that regulate transcription or translation by hybridizing to DNA or RNA and inhibiting and/or preventing transcription or translation from taking place. Antisense molecules include nucleic acid molecules and derivatives and analogs thereof. Antisense molecules hybridize to DNA or RNA in the same manner as complementary nucleotide sequences do regardless of whether or not the antisense molecule is a nucleic acid molecule or a derivative or analog. Antisense molecules may inhibit or prevent transcription or translation of genes whose expression is linked to cancer.

As used herein, the term "GCC immunogen" is meant to refer to GCC protein or a fragment thereof or a protein that comprises the same or a haptenized product thereof; cells and particles which display at least one GCC epitope, and haptenized cells and haptenized particles which display at least one GCC epitope.

As used herein, the term "recombinant expression vector" is meant to refer to a plasmid, phage, viral particle or other vector which, when introduced into an appropriate host, contains the necessary genetic elements to direct expression of the coding sequence that encodes the protein. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences.

As used herein, the term "illegitimate transcription" is meant to refer to the low level or background expression of tissue-specific genes in cells from other tissues. The phenomenon of illegitimate transcription thus provides copies of mRNA for a tissue specific transcript in other tissues. If detection techniques used to detect gene expression are sufficiently sensitive to detect illegitimate transcription, the expression level of the transcript in negative samples due to illegitimate transcription must be discounted using controls and/or quantitative assays and/or other means to eliminate the incidence of false positive due to illegitimate transcription. Alternatively, detection of evidence of GCC gene expression in sample is achieved without detecting GCC gene transcript present due to illegitimate transcription. This is accomplished using techniques which are not sufficiently sensitive to detect the GCC gene transcript present due to illegitimate transcription which is present as background.

U.S. Pat. No. 5,518,888, issued May 21, 1996, U.S. Pat. No. 5,601,990 issued Feb. 11, 1997, U.S. Pat. No. 6,060,037 issued Apr. 26, 2000, U.S. Pat. No. 5,962,220 issued Oct. 5, 1999, U.S. Pat. No. 5,879,656 issued Mar. 9, 1999, and U.S. patent application Ser. No. 09/180,237 filed Mar. 12, 1997, relate to targeting ST receptors to treat, image, detect and vaccinate against metastasized colorectal cancer. It has now been discovered that primary and metastatic stomach and esophageal cancer cells express ST receptors (GCC). Accordingly, the compositions and methods described in the above-listed patents and application can be used to treat, image, detect and vaccinate against primary and metastatic stomach and esophageal cancer. The present invention adapts the earlier invention as related to metastasized colorectal cancer to treat, image, detect and vaccinate against primary and metastatic stomach and esophageal cancer.

GCC

Carcinomas derived from the colorectal cells, stomach or esophagus express GCC. The expression of GCC by such tumors enables this protein and its mRNA to be a specific biomarker for the presence of cancer cells in extra-intestinal tissues and blood. Indeed, this characteristic permits the detection of GCC mRNA by RT-PCR analysis to be a diagnostic test to stage patients with colorectal, stomach or esophageal cancer and follow patients after surgery for evidence of recurrent disease in their blood as well as to detect colorectal, stomach and esophageal cancers. Further, the GCC may be targeted with a ligand conjugated to an active agent in order to deliver the active agent to tumor cells in vivo.

U.S. Pat. No. 5,518,888 issued May 21, 1996 to Waldman, PCT application PCT/US94/12232 filed Oct. 26, 1994, U.S. application Ser. No. 08/467,920 filed Jun. 6, 1995, and U.S. application Ser. No. 08/583,447 filed Jan. 5, 1996, which are each incorporated herein by reference, disclose that metastasized colorectal tumors can be targeted for delivery of active compounds by targeting ST receptors (also referred to as guanylin cyclase C or GCC). The presence of ST receptors on cells outside of the intestinal tract as a marker for colorectal cancer allows for the screening, identification and treatment of individuals with metastasized colorectal tumors. ST receptors may also be used to target delivery of gene therapeutics and antisense compounds to colorectal cells.

U.S. Pat. No. 5,601,990 issued Feb. 11, 1997 to Waldman, PCT application PCT/US94/12232 filed Oct. 26, 1994, and PCT application PCT/US97/07467 filed May 2, 1997, which are each incorporated herein by reference, disclose that detection of evidence of expression of ST receptors in samples of tissue and body fluid from outside the intestinal track indicate metastasized colorectal cancer.

PCT application PCT/US97/07565 filed May 2, 1997, which is incorporated herein by reference, disclose that immunogens with epitopes that can be targeted by antibodies that react with ST receptors can be used in vaccines compositions useful as prophylactic and therapeutic antimetastatic colorectal cancer compositions.

It has been discovered that, in addition to normal colon cells, to primary and to metastasized colon, stomach and esophageal carcinoma cells also express GCC. Normal stomach and esophageal cells do not express GCC. Thus, the present invention provides the use of GCC as a specific molecular diagnostic marker for the diagnosis, staging, and post-operative surveillance of patients with primary and metastasized stomach and esophageal cancer.

Detection of the expression of GCC employing molecular techniques, including, but not limited to, RT-PCR, can be employed to diagnose and stage patients, follow the development of recurrence after surgery and/or remission, and, potentially, screen normal people for the development of colorectal, stomach or esophageal cancer.

GCC is unique in that it is only expressed in normal intestinal cells. Mucosal cells lining the intestine are joined together by tight junctions which form a barrier against the passage of intestinal contents into the blood stream and components of the blood stream into the intestinal lumen. Therefore, the apical location of cells expressing GCC results in the isolation of such cells from the circulatory system so that they may be considered to exist separate from the rest of the body; essentially the "outside" of the body. Therefore, the rest of the body is considered "outside" the intestinal tract. Compositions administered "outside" the intestinal tract are maintained apart and segregated from the only cells which normally express GCC. Conversely, tissue samples taken from tissue outside of the intestinal tract do not normally contain cells which express GCC.

In individuals suffering from colorectal cancer, the cancer cells are often derived from cells that produce and display the GCC and these cancer cells continue to produce GCC. It has been observed that GCC is expressed by colorectal cancer cells. Likewise, GCC is expressed by stomach and esophageal cancer cells.

The expression of GCC by colorectal tumor cells provides a detectable target for in vitro screening, monitoring and staging as well as a target for in vivo delivery of conjugated compositions that comprise active agents for the imaging and treatment. GCC can also serve as targets for vaccines which may be used to protect against metastasized colorectal cancer or to treat individuals with metastasized colorectal cancer.

The expression of GCC by stomach and esophageal tumor cells provides a detectable target for in vitro screening, monitoring and staging as well as a target for in vivo delivery of conjugated compositions that comprise active agents for the imaging and treatment. GCC can also serve as targets for vaccines which may be used to protect against primary and metastatic stomach and esophageal cancer or to treat individuals with primary and metastatic stomach and esophageal cancer.

In Vitro Diagnostics

According to some embodiments of the invention, compositions, kits and in vitro methods are provided for screening, diagnosing and analyzing patients and patient samples to detect evidence of GCC expression by cells outside of the intestinal tract wherein the expression of GCC may be suggestive of metastasized colorectal cancer or primary or metastatic stomach or esophageal cancer. In patients suspected of having primary or metastatic stomach or esophageal cancer evidence of GCC expression by cells outside of the intestinal tract is indicative of primary or metastatic stomach or esophageal cancer and can be used in the diagnosis, monitoring and staging of such patients. Furthermore, the present invention relates to methods, compositions and kits useful in the in vitro screening, and analysis of patient and patient samples to detect evidence of GCC expression by tumor cells outside of the intestinal tract wherein the presence of cells that express GCC suggests or confirms that a tumor is of colorectal or stomach or esophageal cancer origin. In an additional aspect of the invention, compositions, kits and methods are provided which are useful to visualize primary or metastatic stomach or esophageal cancer cells.

In vitro screening and diagnostic compositions, methods and kits can be used in the monitoring of individuals who are in high risk groups for stomach or esophageal cancer such as those who have been diagnosed with localized disease and/or metastasized disease and/or those who are genetically linked to the disease. In vitro screening and diagnostic compositions, methods and kits can be used in the monitoring of individuals who are undergoing and/or have been treated for primary stomach or esophageal cancer to determine if the cancer has metastasized. In vitro screening and diagnostic compositions, methods and kits can be used in the monitoring of individuals who are undergoing and/or have been treated for stomach or esophageal cancer to determine if the cancer has been eliminated. In vitro screening and diagnostic compositions, methods and kits can be used in the monitoring of individuals who are otherwise susceptible, i.e. individuals who have been identified as genetically predisposed such as by genetic screening and/or family histories. Advancements in the understanding of genetics and developments in technology as well as epidemiology allow for the determination of probability and risk assessment an individual has for developing stomach or esophageal cancer. Using family health histories and/or genetic screening, it is possible to estimate the probability that a particular individual has for developing certain types of cancer including stomach or esophageal cancer. Those individuals that have been identified as being predisposed to developing a particular form of cancer can be monitored or screened to detect evidence of stomach or esophageal cancer. Upon discovery of such evidence, early treatment can be undertaken to combat the disease. Accordingly, individuals who are at risk for developing stomach or esophageal cancer may be identified and samples may be isolated form such individuals. The invention is particularly useful for monitoring individuals who have been identified as having family medical histories which include relatives who have suffered from stomach or esophageal cancer. Likewise, the invention is particularly useful to monitor individuals who have been diagnosed as having stomach or esophageal cancer and, particularly those who have been treated and had tumors removed and/or are otherwise experiencing remission including those who have been treated for stomach or esophageal cancer.

In vitro screening and diagnostic compositions, methods and kits can be used in the analysis of tumors. Expression of GCC is a marker for cell type and suggests the origin of adenocarcinoma of unconfirmed origin suspected of being gastric or esophageal in origin may be stomach or esophageal tumors. Detection of GCC expression can also be used to assist in an initial diagnosis of stomach or esophageal cancer or to confirm such diagnosis. Tumors believed to be stomach or esophageal in origin can be confirmed as such using the compositions, methods and kits of the invention.

In vitro screening and diagnostic compositions, kits and methods of the invention can be used to analyze tissue samples from the stomach or esophagus to identify primary stomach or esophageal cancer.

According to the invention, compounds are provided which bind to GCC gene transcript or protein. Normal tissue in the body does not have GCC transcript or protein except cells of the intestinal tract. The expression of GCC is a marker for cell type and is useful in the identification of stomach or esophageal cancer in extra-intestinal samples.

In some embodiments of the invention, non-colorectal tissue and fluid samples or tumor samples may be screened to identify the presence or absence of GCC protein. Techniques such as ELISA assays and Western blots may be performed to determine whether GCC is present in a sample.

In some embodiments of the invention, non-colorectal tissue and fluid samples or tumor samples may be screened to identify whether GCC are being expressed in cells outside of the colorectal tract by detecting the presence or absence of GCC gene transcript. The presence of GCC gene transcript or cDNA generated therefrom can be determined using techniques such as PCR amplification, branched oligonucleotide technology, Northern Blots (mRNA), Southern Blots (cDNA), or oligonucleotide hybridization.

In some embodiments of the invention, cells of non-colorectal tissue samples or tumor samples may be examined to identify the presence or absence of GCC proteins. Techniques such as immunohistochemistry blots may be performed on tissue sections to determine whether GCC are present in a sample.

In some embodiments of the invention, cells of non-colorectal tissue samples or tumor samples may be examined to determine whether GCC are being expressed in cells outside of the colorectal track by detecting the presence or absence of the GCC gene transcript. The presence of the GCC gene transcript or cDNA generated therefrom in cells from tissue sections can be determined using techniques such as in situ hybridization.

The presence of GCC in non-colorectal tissue and fluid samples or on cells from non-colorectal tissue samples suggests possible stomach or esophageal cancer. The presence of GCC in a tumor sample or on tumor cells suggests that the tumor may be stomach or esophageal in origin. The presence of the GCC gene transcript in non-colorectal tissue and fluid samples or in cells from non-colorectal tissue samples suggests possible stomach or esophageal cancer. The presence of the GCC gene transcript in tumor samples and tumor cells suggests that the tumor may be stomach or esophageal in origin.

Samples may be obtained from resected tissue or biopsy material including needle biopsy. Tissue section preparation for surgical pathology may be frozen and prepared using standard techniques. Immunohistochemistry and in situ hybridization binding assays on tissue sections are performed in fixed cells. Extra-intestinal samples may be homogenized by standard techniques such as sonication, mechanical disruption or chemical lysis such as detergent lysis. It is also contemplated that tumor samples in body fluids such as blood, urine, lymph fluid, cerebral spinal fluid, amniotic fluid, vaginal fluid, semen and stool samples may also be screened to determine if such tumors are colorectal, stomach or esophageal in origin.

Non-colorectal tissue samples may be obtained from any tissue except those of the colorectal tract. i.e. the intestinal tract below the small intestine (i.e. the large intestine (colon), including the cecum, ascending colon, transverse colon, descending colon, and sigmoid colon, and rectum) and additionally the duodenum and small intestine (jejunum and ileum). The normal cells of all tissue except those of the colorectal tract do not express GCC. Thus if GCC protein or the GCC gene transcript are detected in non-colorectal samples, the possible presence of colorectal, stomach or esophageal cancer cells is suggested. In some preferred embodiments, the tissue samples are lymph nodes.

Tissue samples may be obtained by standard surgical techniques including use of biopsy needles. One skilled in the art would readily appreciate the variety of test samples that may be examined for GCC and recognize methods of obtaining tissue samples.

Tissue samples may be homogenized or otherwise prepared for screening for the presence of GCC by well known techniques such as sonication, mechanical disruption, chemical lysis such as detergent lysis or combinations thereof.

Examples of body fluid samples include blood, urine, lymph fluid, cerebral spinal fluid, amniotic fluid, vaginal fluid and semen. In some preferred embodiments, blood is used as a sample of body fluid. Cells may be isolated from fluid sample such as centrifugation. One skilled in the art would readily appreciate the variety of test samples that may be examined for GCC. Test samples may be obtained by such methods as withdrawing fluid with a syringe or by a swab. One skilled in the art would readily recognize other methods of obtaining test samples.

In an assay using a blood sample, the blood plasma may be separated from the blood cells. The blood plasma may be screened for GCC including truncated proteins which are released into the blood when one or more GCC are cleaved from or sloughed off from tumor cells. In some embodiments, blood cell fractions are screened for the presence of stomach or esophageal tumor cells. In some embodiments, lymphocytes present in the blood cell fraction are screened by lysing the cells and detecting the presence of GCC protein or the GCC gene transcript which may be present as a result of the presence of any stomach or esophageal tumor cells that may have been engulfed by the blood cell. In some preferred embodiments, CD34+ cells are removed prior to isolation of mRNA from samples using commercially available immuno-columns.

Aspects of the present invention include various methods of determining whether a sample contains cells that express GCC by nucleotide sequence-based molecular analysis to detect the GCC gene transcript. Several different methods are available for doing so including those using Polymerase Chain Reaction (PCR) technology, branched oligonucleotide technology, Northern blot technology, oligonucleotide hybridization technology, and in situ hybridization technology.

The invention relates to oligonucleotide probes and primers used in the methods of identifying the GCC gene transcript and to diagnostic kits which comprise such components.

The mRNA sequence-based methods for detect the GCC gene transcript include but are not limited to polymerase chain reaction technology, branched oligonucleotide technology, Northern and Southern blot technology, in situ hybridization technology and oligonucleotide hybridization technology.

The methods described herein are meant to exemplify how the present invention may be practiced and are not meant to limit the scope of invention. It is contemplated that other sequence-based methodology for detecting the presence of the GCC gene transcript in non-colorectal samples may be employed according to the invention.

A preferred method to detecting the GCC gene transcript in genetic material derived from non-colorectal samples uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. No. 4,683,202, U.S. Pat. No. 4,683,195, U.S. Pat. No. 4,965,188 and U.S. Pat. No. 5,075,216, which are each incorporated herein by reference describe methods of performing PCR. PCR may be routinely practiced using Perkin Elmer Cetus GENE AMP RNA PCR kit, Part No. N808-0017.

PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the same small fragment of nucleic acid, exponential amplification of a specific double-stranded size product results. If only a single primer hybridizes to the nucleic acid fragment, linear amplification produces single-stranded products of variable length.

PCR primers can be designed routinely by those having ordinary skill in the art using sequence information. The nucleotide sequence of the GCC gene transcript is set forth in SEQ ID NO:1. To perform this method, RNA is extracted from cells in a sample and tested or used to make cDNA using well known methods and readily available starting materials. Those having ordinary skill in the art can readily prepare PCR primers. A set of primers generally contains two primers. When performing PCR on extracted mRNA or cDNA generated therefrom, if the GCC gene transcript or cDNA generated therefrom is present, multiple copies of the mRNA or cDNA will be made. If it is not present, PCR will not generate a discrete detectable product. Primers are generally 8-50 nucleotides, preferably about 15-35 nucleotides, more preferably 18-28 nucleotides, which are identical or complementary to and therefor hybridize to the GCC gene transcript or cDNA generated therefrom. In preferred embodiments, the primers are each 15-35 nucleotide, more preferably 18-28 nucleotide fragments of SEQ ID NO:1. The primer must hybridize to the sequence to be amplified. Typical primers are 18-28 nucleotides in length and are generally have 50% to 60% G+C composition. The entire primer is preferably complementary to the sequence it must hybridize to. Preferably, primers generate PCR products 100 base pairs to 2000 base pairs. However, it is possible to generate products of 50 to up to 10 kb and more. If mRNA is used as a template, the primers must hybridize to mRNA sequences. If cDNA is used as a template, the primers must hybridize to cDNA sequences.

The mRNA or cDNA is combined with the primers, free nucleotides and enzyme following standard PCR protocols. The mixture undergoes a series of temperature changes. If the GCC gene transcript or cDNA generated therefrom is present, that is, if both primers hybridize to sequences on the same molecule, the molecule comprising the primers and the intervening complementary sequences will be exponentially amplified. The amplified DNA can be easily detected by a variety of well known means. If no GCC gene transcript or cDNA generated therefrom is present, no PCR product will be exponentially amplified. The PCR technology therefore provides an extremely easy, straightforward and reliable method of detecting the GCC gene transcript in a sample.

PCR product may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotide which are useful as primers for performing PCR methods to amplify the GCC gene transcript or cDNA generated therefrom.

According to the invention, diagnostic kits can be assembled which are useful to practice methods of detecting the presence of the GCC gene transcript or cDNA generated therefrom in non-colorectal samples. Such diagnostic kits comprise oligonucleotide which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the GCC gene transcript or cDNA generated therefrom. Additional components in some kits include instructions for carrying out the assay. Additionally the kit may optionally comprise depictions or photographs that represent the appearance of positive and negative results. Positive and negative controls may also be provided.

PCR assays are useful for detecting the GCC gene transcript in homogenized tissue samples and cells in body fluid samples. It is contemplated that PCR on the plasma portion of a fluid sample could be used to detect the GCC gene transcript.

Another method of determining whether a sample contains cells expressing GCC is by branched chain oligonucleotide hybridization analysis of mRNA extracted from a sample. Branched chain oligonucleotide hybridization may be performed as described in U.S. Pat. No. 5,597,909, U.S. Pat. No. 5,437,977 and U.S. Pat. No. 5,430,138, which are each incorporated herein by reference. Reagents may be designed following the teachings of those patents and that sequence of the GCC gene transcript.

Another method of determining whether a sample contains cells expressing GCC is by Northern Blot analysis of mRNA extracted from a non-colorectal sample. The techniques for performing Northern blot analyses are well known by those having ordinary skill in the art and are described in Sambrook, J. et al., (1989) *Molecular Cloning, A Laboratory Manual*, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

The mRNA is extracted using poly dT columns and the material is separated by electrophoresis and, for example, transferred to nitrocellulose paper. Labeled probes made from an isolated specific fragment or fragments can be used to visualize the presence of a complementary fragment fixed to the paper. Probes useful to identify mRNA in a Northern Blot have a nucleotide sequence that is complementary to the GCC gene transcript. Those having ordinary skill in the art could use the sequence information in SEQ ID NO:1 to design such probes or to isolate and clone the GCC gene transcript or cDNA generated therefrom to be used as a probe. Such probes are at least 15 nucleotides, preferably 30-200, more preferably 40-100 nucleotide fragments and may be the entire GCC gene transcript.

According to the invention, diagnostic kits can be assembled which are useful to practice methods of detecting the presence of the GCC gene transcript in non-colorectal samples by Northern blot analysis. Such diagnostic kits comprise oligonucleotide which are useful as probes for hybridizing to the mRNA. The probes may be radiolabeled. It is preferred that diagnostic kits according to the present invention comprise a container comprising a size marker to be run as a standard on a gel. It is preferred that diagnostic kits according to the present invention comprise a container comprising a positive control which will hybridize to the probe. Additional components in some kits include instructions for carrying out the assay. Additionally the kit may optionally comprise depictions or photographs that represent the appearance of positive and negative results.

Northern blot analysis is useful for detecting the GCC gene transcript in homogenized tissue samples and cells in body fluid samples. It is contemplated that PCR on the plasma portion of a fluid sample could be used to detect the GCC gene transcript.

Another method of detecting the presence of the GCC gene transcript by oligonucleotide hybridization technology. Oligonucleotide hybridization technology is well known to those having ordinary skill in the art. Briefly, detectable probes which contain a specific nucleotide sequence that will hybridize to nucleotide sequence of the GCC gene transcript. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences.

Probes useful in oligonucleotide assays at least 18 nucleotides of complementary DNA and may be as large as a complete complementary sequence to the GCC gene transcript. In some preferred embodiments the probes of the invention are 30-200 nucleotides, preferably 40-100 nucleotides.

One having ordinary skill in the art, using the sequence information disclosed in SEQ ID NO:1 can design probes useful in the invention. Hybridization conditions can be routinely optimized to minimize background signal by non-fully complementary hybridization. In some preferred embodiments, the probes are full length clones. Probes are at least 15 nucleotides, preferably 30-200, more preferably 40-100 nucleotide fragments and may be the entire GCC gene transcript.

The present invention includes labeled oligonucleotide which are useful as probes for performing oligonucleotide hybridization. The labeled probes of the present invention are labeled with radiolabeled nucleotides or are otherwise detectable by readily available nonradioactive detection systems.

According to the invention, diagnostic kits can be assembled which are useful to practice oligonucleotide hybridization methods of the invention. Such diagnostic kits comprise a labeled oligonucleotide which encodes portions of the GCC gene transcript. It is preferred that labeled probes of the oligonucleotide diagnostic kits according to the present invention are labeled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample. Additional components in some kits include instructions for carrying out the assay. Additionally the kit may optionally comprise depictions or photographs that represent the appearance of positive and negative results.

Oligonucleotide hybridization techniques are useful for detecting the GCC gene transcript in homogenized tissue samples and cells in body fluid samples. It is contemplated that PCR on the plasma portion of a fluid sample could be used to detect the GCC gene transcript.

The present invention relates to in vitro kits for evaluating samples of tumors to determine whether or not they are stomach or esophageal in origin and to reagents and compositions useful to practice the same. In some embodiments of the invention, tumor samples may be isolated from individuals undergoing or recovery from surgery to remove tumors in the stomach or esophagus, tumors in other organs or biopsy material. The tumor sample is analyzed to identify the presence or absence of the GCC gene transcript. Techniques such as immunohistochemistry assays may be performed to determine whether GCC are present in cells in the tumor sample. The presence of mRNA that encodes the GCC protein or cDNA generated therefrom can be determined using techniques such as in situ hybridization, immunohistochemistry and in situ ST binding assay.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them.

Probes useful in oligonucleotide assays at least 18 nucleotides of complementary DNA and may be as large as a complete complementary sequence to the GCC gene transcript. In some preferred embodiments the probes of the invention are 30-200 nucleotides, preferably 40-100 nucleotides.

One having ordinary skill in the art, using the sequence information set forth in SEQ ID NO:1 can design probes useful in in situ hybridization technology to identify cells that express GCC. Probes preferably hybridizes to a nucleotide sequence that corresponds to the GCC gene transcript. Hybridization conditions can be routinely optimized to minimize background signal by non-fully complementary hybridization. Probes preferably hybridize to the full length GCC gene transcript. Probes are at least 15 nucleotides, preferably 30-200, more preferably 40-100 nucleotide fragments and may be the GCC gene transcript, more preferably 18-28 nucleotide fragments of the GCC gene transcript.

The probes are fully complementary and do not hybridize well to partially complementary sequences. For in situ hybridization according to the invention, it is preferred that the probes are detectable by fluorescence. A common procedure is to label probe with biotin-modified nucleotide and then detect with fluorescently tagged avidin. Hence, probe does not itself have to be labeled with florescent but can be subsequently detected with florescent marker.

The present invention includes labeled oligonucleotide which are useful as probes for performing oligonucleotide hybridization. That is, they are fully complementary with mRNA sequences but not genomic sequences. The labeled probes of the present invention are labeled with radiolabeled nucleotides or are otherwise detectable by readily available nonradioactive detection systems.

The present invention relates to probes useful for in situ hybridization to identify cells that express GCC.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences but not genomic sequences. For example, the mRNA sequence includes different exon sequences. It is preferred that labeled probes of the in situ diagnostic kits according to the present invention are labeled with a fluorescent marker.

Immunohistochemistry techniques may be used to identify and essentially stain cells with GCC. Such "staining" allows for analysis of metastatic migration. Anti-GCC antibodies such as those described above of contacted with fixed cells and the GCC present in the cells reacts with the antibodies. The antibodies are detectably labeled or detected using labeled second antibody or protein A to stain the cells.

The techniques described herein for evaluating tumor sections can also be used to analyze tissue sections for samples of lymph nodes as well as other tissues to identify the presence of cells that express GCC. The samples can be prepared and "stained" to detect expression of GCC.

Immunoassay methods may be used in the diagnosis of individuals suffering from stomach or esophageal cancer by detecting presence of GCC in sample of non-colorectal tissue or body fluid from an individuals suspected of having or being susceptible to stomach or esophageal cancer using antibodies which were produced in response to exposure to such GCC protein. Moreover, immunoassay methods may be used to identify individuals suffering from stomach or esophageal cancer by detecting presence of GCC in sample of tumor using antibodies which were produced in response to exposure to such GCC protein.

The antibodies are preferably monoclonal antibodies. The antibodies are preferably raised against GCC made in human cells. Immunoassays are well known and there design may be routinely undertaken by those having ordinary skill in the art. Those having ordinary skill in the art can produce monoclonal antibodies which specifically bind to GCC and are useful in methods and kits of the invention using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins. It is within the scope of the present invention to include Fabs, recombinant Fabs, F(Ab)2s, recombinant F(Ab)2s which specifically bind to GCC translation products in place of antibodies.

Briefly, GCC protein is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the GCC, the hybridoma which produces them is cultured to produce a continuous supply of anti-GCC specific antibodies.

The antibodies are preferably monoclonal antibodies. The antibodies are preferably raised against GCC made in human cells.

The means to detect the presence of a protein in a test sample are routine and one having ordinary skill in the art can detect the presence or absence of a protein or an antibody using well known methods. One well known method of detecting the presence of a protein is an immunoassay. One having ordinary skill in the art can readily appreciate the multitude of ways to practice an immunoassay to detect the presence of a GCC protein in a sample.

According to some embodiments, immunoassays comprise allowing proteins in the sample to bind a solid phase support such as a plastic surface. Detectable antibodies are then added which selectively binding to the GCC. Detection of the detectable antibody indicates the presence of GCC. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described in *Immunoassays for the 80's*, A. Voller et al., Eds., University Park, 1981, which is incorporated herein by reference.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein, A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, Kirkham, Ed., E. & S. Livingstone, Edinburgh, 1970, pp. 199-206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of GCC in a test sample is an anti-GCC antibody. By "solid phase support" or "support" is intended any material capable of binding proteins. Well-known solid phase supports include glass, polystyrene, polypropylene, polyethylene, destran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of GCC, detectable anti-GCC antibodies are used. Several methods are well known for the detection of antibodies.

One method in which the antibodies can be detectably labeled is by linking the antibodies to an enzyme and subsequently using the antibodies in an enzyme immunoassay (ELA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labeled is through radioactive isotopes and subsequent use in a radioimmunoassay (RIA) (see, for example, Work, T. S. et al., *Laboratory Techniques and Biochemistry in Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^3$H, $^{125}$I, $^{131}$I, $^{35}$S, and $^{14}$C. Preferably $^{125}$I is the isotope. One skilled in the art would readily recognize other radioisotopes which may also be used.

It is also possible to label the antibody with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, Q-phthaldehyde and fluorescamine. One skilled in the art would readily recognize other fluorescent compounds which may also be used.

Antibodies can also be detectably labeled using fluorescence-emitting metals such as $^{152}$Eu, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibody can also be detectably labeled by coupling to a chemiluminescent compound. The presence of the chemiluminescent-labeled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of GCC proteins and no GCC protein, respectively, are added to assays being performed in parallel with the test assay. One skilled in the art would have the necessary knowledge to perform the appropriate controls. In addition, the kit may comprise instructions for performing the assay. Additionally the kit may optionally comprise depictions or photographs that represent the appearance of positive and negative results.

GCC may be produced as a reagent for positive controls routinely. One skilled in the art would appreciate the different manners in which the GCC protein may be produced and isolated.

Antibody composition refers to the antibody or antibodies required for the detection of the protein. For example, the antibody composition used for the detection of a GCC in a test sample comprises a first antibody that binds to the GCC as well as a second or third detectable antibody that binds the first or second antibody, respectively.

To examine a test sample for the presence of a GCC, a standard immunometric assay such as the one described below may be performed. A first anti-GCC antibody, which recognizes a specific portion of GCC, is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from non-specifically binding the microtiter plate. Test sample are subsequently added to the wells and the plate is incubated for a period of time sufficient for binding to occur. The wells are washed with PBS to remove unbound protein. Labeled anti-GCC antibodies, which recognize portions of GCC not recognized by the first antibody, are added to the wells. The plate is incubated for a period of time sufficient for binding to occur and subsequently washed with PBS to remove unbound, labeled anti-GCC antibody. The amount of labeled and bound anti-GCC antibody is subsequently determined by standard techniques.

Kits which are useful for the detection of GCC in a test sample comprise a container comprising anti-GCC antibodies and a container or containers comprising controls. Controls include one control sample which does not contain GCC and/or another control sample which contained the GCC. The anti-GCC antibodies used in the kit are detectable such as being detectably labeled. If the detectable anti-GCC antibody is not labeled, it may be detected by second antibodies or protein A for example which may also be provided in some kits in separate containers. Additional components in some kits include solid support, buffer, and instructions for carrying out the assay. Additionally the kit may optionally comprise depictions or photographs that represent the appearance of positive and negative results.

The immunoassay is useful for detecting GCC in homogenized tissue samples and body fluid samples including the plasma portion or cells in the fluid sample.

Western Blots may be useful in assisting the diagnosis of individuals suffering from stomach or esophageal cancer by detecting presence of GCC of non-colorectal tissue or body fluid. Western blots may also be used to detect presence of GCC in sample of tumor from an individual suffering from cancer. Western blots use detectable anti-GCC-antibodies to bind to any GCC present in a sample and thus indicate the presence of the receptor in the sample.

Western blot techniques, which are described in Sambrook, J. et al., (1989) *Molecular Cloning: A Laboratory Manual*, Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-GCC antibodies described above are useful in Western blot methods.

Generally, samples are homogenized and cells are lysed using detergent such as Triton-X. The material is then separated by the standard techniques in Sambrook, J. et al., (1989) *Molecular Cloning: A Laboratory Manual*, Cold Spring Harbor Laboratory Press, Cold Spring Harbor, N.Y.

Kits which are useful for the detection of GCC in a test sample by Western Blot comprise a container comprising anti-GCC antibodies and a container or containers comprising controls. Controls include one control sample which does not contain GCC and/or another control sample which contains GCC. The anti-GCC antibodies used in the kit are detectable such as being detectably labeled. If the detectable anti-GCC antibody is not labeled, it may be detected by second antibodies or protein A for example which may also be provided in some kits in separate containers. Additional components in some kits include instructions for carrying out the assay. Additionally the kit may optionally comprise depictions or photographs that represent the appearance of positive and negative results.

Western blots are useful for detecting GCC in homogenized tissue samples and body fluid samples including the plasma portion or cells in the fluid sample.

In Vivo Imaging and Therapeutics

According to some embodiments of the invention, compositions and in vivo methods are provided for detecting, imaging, or treating primary and/or metastatic stomach or esophageal tumors in an individual.

When the conjugated compositions of the present invention are administered outside the intestinal tract such as when administered in the circulatory system, they remain segregated from the cells that line the intestinal tract and will bind only to cells outside the intestinal tract which express GCC. The conjugated compositions will not bind to the normal cells but will bind to primary and/or metastatic stomach or esophageal cells. Thus, the active moieties of conjugated compositions administered outside the intestinal tract are delivered to cells which express GCC such as primary and/or metastatic stomach or esophageal cancer cells.

Therapeutic and diagnostic pharmaceutical compositions useful in the present invention include conjugated compounds that specifically target cells that express GCC. These conjugated compounds include moieties that bind to GCC which do not bind to cells of normal tissue in the body except cells of the intestinal tract since the cells of other tissues do not express GCC.

Unlike normal colorectal cells, cancer cells that express GCC are accessible to substances administered outside the intestinal tract, for example administered in the circulatory system. The only GCC in normal tissue exist in the apical membranes of intestinal mucosa cells and thus effectively isolated from the targeted cancer chemotherapeutics and imaging agents administered outside the intestinal tract by the intestinal mucosa barrier. Thus, primary and/or metastatic stomach or esophageal cancer cells may be targeted by conjugated compounds of the present invention by introducing such compounds outside the intestinal tract such as for example by administering pharmaceutical compositions that comprise conjugated compounds into the circulatory system.

One having ordinary skill in the art can identify individuals suspected of suffering from primary and/or metastatic stomach or esophageal cancer. In those individuals diagnosed with stomach or esophageal cancer, it is not unusual and in some cases standard therapy to suspect metastasis and aggressively attempt to eradicate metastasized cells. The present invention provides pharmaceutical compositions and methods, for imaging and thereby will more definitively diagnose primary and metastastic disease. Further, the present invention provides pharmaceutical compositions comprising therapeutic agents and methods for specifically targeting and eliminating primary and/or metastatic stomach or esophageal cancer cells. Further, the present invention provides pharmaceutical compositions that comprise therapeutics and methods for specifically eliminating primary and/or metastatic stomach or esophageal cancer cells.

The pharmaceutical compositions which comprise conjugated compositions of the present invention may be used to diagnose or treat individuals suffering from primary and/or metastatic stomach or esophageal tumors.

The present invention relies upon the use of a GCC binding moiety in a conjugated composition. The GCC binding moiety is essentially a portion of the conjugated composition which acts as a ligand to a GCC and thus specifically binds to it. The conjugated composition also includes an active moiety which is associated with the GCC binding moiety; the active moiety being an active agent which is either useful to image, target, neutralize or kill the cell.

According to the present invention, the GCC binding moiety is the GCC ligand portion of a conjugated composition. In some embodiments, the GCC ligand is an antibody.

In some preferred embodiments, conjugated compounds comprise GCC binding moieties that comprise an anti-GCC antibody.

It is preferred that the GCC ligand used as the GCC binding moiety be as small as possible. Thus it is preferred that the GCC ligand be a non-peptide small molecule or small peptide, preferably less than 25 amino acids, more preferably less than 20 amino acids. In some embodiments, the GCC ligand which constitute the GCC binding moiety of a conjugated composition is less than 15 amino acids. GCC binding peptide comprising less than 10 amino acids and GCC binding peptide less than 5 amino acids may be used as GCC binding moieties according to the present invention. It is within the scope of the present invention to include larger molecules which serve as GCC binding moieties including, but not limited to molecules such as antibodies which specifically bind to GCC.

GCC ligands useful as GCC binding moieties may be identified using various well known combinatorial library screening technologies such as those set forth in Example 1 herein.

An assay may be used to test both peptide and non-peptide compositions to determine whether or not they are GCC ligands or, to test conjugated compositions to determine if they possess GCC-binding activity. Such compositions that specifically bind to GCC can be identified by a competitive binding assay using antibodies known to bind to the GCC. The competitive binding assay is a standard technique in pharmacology which can be readily performed by those having ordinary skill in the art using readily available starting materials.

GCC may be produced synthetically, recombinantly or isolated from natural sources.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Antibodies against GCC may be routinely produced and used in competition assays to identify GCC ligands or as starting materials for conjugated compounds according to the invention.

According to the present invention, the active moiety may be a therapeutic agent or an imaging agent. One having ordinary skill in the art can readily recognize the advantages of being able to specifically target cancer cells with an GCC ligand and conjugate such a ligand with many different active agents.

Chemotherapeutics useful as active moieties which when conjugated to a GCC binding moiety are specifically delivered to cells that express GCC such as stomach or esophageal cancer cells, are typically small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of chemotherapeutics include common cytotoxic or cytostatic drugs such as for example: methotrexate (amethopterin), doxorubicin (adrimycin), daunonrbicin, cytosinarabinoside, etoposide, 5-4 fluorouracil, melphalan, chlorambucil, and other nitrogen mustards (e.g. cyclophosphamide), cis-platinnm, vindesine (and other vinca alkaloids), mitomycin and bleomycin. Other chemotherapeutics include: purothionin (barley flour oligopeptide), macromomycin. 1,4-benzoquinone derivatives and trenimon.

Toxins are useful as active moieties. When a toxin is conjugated to a GCC binding moiety, the conjugated composition is specifically delivered to a cell that expresses GCC such as stomach or esophageal cancer cells by way of the GCC binding moiety and the toxin moiety kills the cell. Toxins are generally complex toxic products of various organisms including bacteria, plants, etc. Examples of toxins include but are not limited to: ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saponn (SAP), modeccin, viscumin and volkensin. As discussed above, when protein toxins are employed with GCC binding peptides, conjugated compositions may be produced using recombinant DNA techniques. Briefly, a recombinant DNA molecule can be constructed which encodes both the GCC ligand and the toxin on a chimeric gene. When the chimeric gene is expressed, a fusion protein is produced which includes a GCC binding moiety and an active moiety. Protein toxins are also useful to form conjugated compounds with GCC binding peptides through non-peptidyl bonds.

In addition, there are other approaches for utilizing active agents for the treatment of cancer. For example, conjugated compositions may be produced which include a GCC binding moiety and an active moiety which is an active enzyme. The GCC binding moiety specifically localizes the conjugated composition to the tumor cells. An inactive prodrug which can be converted by the enzyme into an active drug is administered to the patient. The prodrug is only converted to an active drug by the enzyme which is localized to the tumor. An example of an enzyme/prodrug pair includes alkaline phosphataseletoposidepbosphate. In such a case, the alkaline phosphatase is conjugated to a GCC binding ligand. The conjugated compound is administered and localizes at the cancer cell. Upon contact with etoposidephosphate (the prodrug), the etoposidephosphate is converted to etoposide, a chemotherapeutic drug which is taken up by the cancer cell.

Radiosensitizing agents are substances that increase the sensitivity of cells to radiation. Examples of radiosensitizing agents include nitroimidazoles, metronidazole and misonidazole (see: DeVita, V. T. Jr. in *Harrison's Principles of Internal Medicine*, p. 68, McGraw-Hill Book Co., N.Y. 1983, which is incorporated herein by reference). The conjugated compound that comprises a radiosensitizing agent as the active moiety is administered and localizes at the primary and/or metastatic stomach or esophageal cancer cell. Upon exposure of the individual to radiation, the radiosensitizing agent is "excited" and causes the death of the cell.

Radionuclides may be used in pharmaceutical compositions that are useful for radiotherapy or imaging procedures.

Examples of radionuclides useful as toxins in radiation therapy include: $^{47}$Sc, $^{67}$Cu, $^{90}$Y, $^{109}$Pd, $^{123}$I, $^{125}$R, $^{131}$I, $^{186}$Re, $^{188}$Re, $^{199}$Au, $^{211}$At, $^{212}$Pb and $^{212}$B. Other radionuclides which have been used by those having ordinary skill in the art include: $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, all beta negative and/or auger emitters. Some preferred radionuclides include: $^{90}$Y, $^{131}$I $^{211}$At and $^{212}$Pb/$^{212}$Bi.

According to the present invention, the active moieties may be an imaging agent. Imaging agents are useful diagnostic procedures as well as the procedures used to identify the location of cancer cells. Imaging can be performed by many procedures well-known to those having ordinary skill in the art and the appropriate imaging agent useful in such procedures may be conjugated to a GCC ligand by well-known means. Imaging can be performed, for example, by radioscintigraphy, nuclear magnetic resonance imaging (MRI) or computed tomography (CT scan). The most commonly employed radionuclide imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium. Example of radionuclides useful in imaging procedures include: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi.

It is preferred that the conjugated compositions be non-immunogenic or immunogenic at a very low level. Accordingly, it is preferred that the GCC binding moiety be a small, poorly immunogenic or non-immunogenic peptide or a non-peptide. The GCC binding moiety may be a humanized or primatized antibody or a human antibody.

GCC ligands are conjugated to active agents by a variety of well-known techniques readily performed without undue experimentation by those having ordinary skill in the art. The technique used to conjugate the GCC ligand to the active agent is dependent upon the molecular nature of the GCC ligand and the active agent. After the GCC ligand and the active agent are conjugated to form a single molecule, assays may be performed to ensure that the conjugated molecule retains the activities of the moieties. The competitive binding assay described above may be used to confirm that the GCC binding moiety retains its binding activity as a conjugated compound. Similarly, the activity of the active moiety may be tested using various assays for each respective type of active agent. Radionuclides retain them activity, i.e. their radioactivity, irrespective of conjugation. With respect to active agents which are toxins, drugs and targeting agents, standard assays to demonstrate the activity of unconjugated forms of these compounds may be used to confirm that the activity has been retained.

Conjugation may be accomplished directly between the GCC ligand and the active agent or linking, intermediate molecular groups may be provided between the GCC ligand and the active agent. Crosslinkers are particularly useful to facilitate conjugation by providing attachment sites for each moiety. Crosslinkers may include additional molecular groups which serve as spacers to separate the moieties from each other to prevent either from interfering with the activity of the other.

One having ordinary skill in the art may conjugate a GCC ligand to a chemotherapeutic drug using well-known techniques. For example, Magerstadt, M. *Antibody Conjugates and Malignant Disease.* (1991) CRC Press, Boca Raton, USA, pp. 110-152) which is incorporated herein by reference, teaches the conjugation of various cytostatic drugs to amino acids of antibodies. Such reactions may be applied to conjugate chemotherapeutic drugs to GCC ligands, including anti-GCC antibodies, with an appropriate linker. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of an antibody. For example, one procedure for crosslinking GCC ligands which have a free amino group to active agents which have a free amino group such as methotrexate, doxorubicin, daunorubicin, cytosinarabinoside, cis-platin, vindesine, mitomycin and bleomycin, or alkaline phosphatase, or protein- or peptide-based toxin employs homobifunctional succinimidyl esters, preferably with carbon chain spacers such as disuccinimidyl suberate (Pierce Co, Rockford, Ill.). In the event that a cleavable conjugated compound is required, the same protocol would be employed utilizing 3,3'-dithiobis(sulfosuccinimidylpropionate; Pierce Co.).

In order to conjugate a GCC ligand that is a peptide or protein to a peptide-based active agent such as a toxin, the GCC ligand and the toxin may be produced as a single, fusion protein either by standard peptide synthesis or recombinant DNA technology, both of which can be routinely performed by those having ordinary skill in the art. Alternatively, two peptides, the GCC ligand peptide and the peptide-based toxin may be produced and/or isolated as separate peptides and conjugated using crosslinkers. As with conjugated compositions that contain chemotherapeutic drugs, conjugation of GCC binding peptides and toxins can exploit the ability to modify the single free amino group of a GCC binding peptide while preserving the receptor-binding function of this molecule.

One having ordinary skill in the art may conjugate a GCC ligand to a radionuclide using well-known techniques. For example, Magerstadt, M. (1991) *Antibody Conjugates And Malignant Disease*, CRC Press, Boca Raton, Fla.; and Barchel, S. W. and Rhodes, B. H., (1983) *Radioimaging and Radiotherapy*, Elsevier, N.Y., NY, each of which is incorporated herein by reference, teach the conjugation of various therapeutic and diagnostic radionuclides to amino acids of antibodies.

The present invention provides pharmaceutical compositions that comprise the conjugated compounds of the invention and pharmaceutically acceptable carriers or diluents. The pharmaceutical composition of the present invention may be formulated by one having ordinary skill in the art. Suitable pharmaceutical carriers are described in *Remington's Pharmaceutical Sciences*, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents. Pharmaceutical compositions are preferably sterile and pyrogen free.

The conjugated compositions of the invention can be, for example, formulated as a solution, suspension or emulsion in association with a pharmaceutically acceptable parenteral vehicle. Examples of such vehicles are water, saline, Ringer's solution, dextrose solution, and 5% human serum albumin. Liposomes may also be used. The vehicle may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the conjugated composition to reach the targeted cells. In some embodiments, routes of administration include those selected from the group consisting of intravenous, intraarterial, intraperitoneal, local administration into the blood supply of the organ in which the tumor resides or directly into the tumor itself. Intravenous administration is the preferred mode of administration. It may be accomplished with the aid of an infusion pump. In addition to an intraoperative spray, conjugated compounds may be delivered intrathecally, intraventrically, stereotactically, intrahepatically such as via the portal vein, by inhalation, and intrapleurally.

The dosage administered varies depending upon factors such as: the nature of the active moiety; the nature of the conjugated composition; pharmacodynamic characteristics; its mode and mute of administration; age, health, and weight of the recipient; nature and extent of symptoms; kind of concurrent treatment; and frequency of treatment.

Because conjugated compounds are specifically targeted to cells with one or more GCC molecules, conjugated compounds which comprise chemotherapeutics or toxins are administered in doses less than those which are used when the chemotherapeutics or toxins are administered as unconjugated active agents, preferably in doses that contain up to 100 times less active agent. In some embodiments, conjugated compounds which comprise chemotherapeutics or toxins are administered in doses that contain 10-100 times less active agent as an active moiety than the dosage of chemotherapeutics or toxins administered as unconjugated active agents. To determine the appropriate dose, the amount of compound is preferably measured in moles instead of by weight. In that way, the variable weight of different GCC binding moieties does not affect the calculation. Presuming a one to one ratio of GCC binding moiety to active moiety in conjugated compositions of the invention, less moles of conjugated compounds may be administered as compared to the moles of unconjugated compounds administered, preferably up to 100 times less moles.

Typically, chemotherapeutic conjugates are administered intravenously in multiple divided doses.

Up to 20 gm IV/dose of methotrexate is typically administered in an unconjugated form. When methotrexate is administered as the active moiety in a conjugated compound of the invention, there is a 10- to 100-fold dose reduction. Thus, presuming each conjugated compound includes one molecule of methotrexate conjugated to one GCC binding moiety, of the total amount of conjugated compound administered, up to about 0.2-2.0 g of methotrexate is present and therefore administered. In some embodiments, of the total amount of conjugated compound administered, up to about 200 mg-2 g of methotrexate is present and therefore administered.

To dose conjugated compositions comprising GCC binding moieties linked to active moieties that are radioisotopes in pharmaceutical compositions useful as imaging agents, it is presumed that each GCC binding moiety is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. Typically 0.1-100 millicuries per dose of imaging agent, preferably 1-10 millicuries, most often 2-5 millicuries are administered. Thus, pharmaceutical compositions according to the present invention useful as imaging agents which comprise conjugated compositions comprising a GCC binding moiety and a radioactive moiety comprise 0.1-100 millicuries, in some embodiments preferably 1-10 millicuries, in some embodiments preferably 2-5 millicuries, in some embodiments more preferably 1-5 millicuries. Examples of dosages include: $^{131}$I=between about 0.1-100 millicuries per dose, in some embodiments preferably 1-10 millicuries, in some embodiments 2-5 millicuries, and in some embodiments about 4 millicuries; $^{111}$In=between about 0.1-100 millicuries per dose, in some embodiments preferably 1-10 millicuries, in some embodiments 1-5 millicuries, and in some embodiments about 2 millicuries; $^{99m}$Tc=between about 0.1-100 millicuries per dose, in some embodiments preferably 5-75 millicuries, in some embodiments 10-50 millicuries, and in some embodiments about 27 millicuries. Weasels B. W. and R. D. Rogus (1984) *Med. Phys.* 11:638 and Kwok, C. S. et al. (1985) *Med. Phys.* 12:405, both of which are incorporated herein by reference, disclose detailed dose calculations for diagnostic and therapeutic conjugates which may be used in the preparation of pharmaceutical compositions of the present invention which include radioactive conjugated compounds.

One aspect of the present invention relates to a method of treating individuals suspected of suffering from primary and/or metastatic stomach or esophageal cancer. Such individuals may be treated by administering to the individual a pharmaceutical composition that comprises a pharmaceutically acceptable carrier or diluent and a conjugated compound that comprises a GCC-binding moiety and an active moiety wherein the active moiety is a radiostable therapeutic agent. In some embodiments of the present invention, the pharmaceutical composition comprises a pharmaceutically acceptable carrier or diluent and a conjugated compound that comprises a GCC binding moiety and an active moiety wherein the active moiety is a radiostable active agent and the GCC binding moiety is an antibody. In some embodiments of the present invention, the pharmaceutical composition comprises a pharmaceutically acceptable carrier or diluent and a conjugated compound that comprises a GCC binding moiety and an active moiety wherein the active moiety is a radiostable active agent selected from the group consisting of: methotrexate, doxorubicin, daunorubicia, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. The individual being treated may be diagnosed as having metastasized stomach or esophageal cancer or may be diagnosed as having primary stomach or esophageal cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on cancer cells without causing lethal side effects on the individual.

One aspect of the present invention relates to a method of treating individuals suspected of suffering from primary and/or metastatic stomach or esophageal cancer. Such individuals may be treated by administering to the individual a pharmaceutical composition that comprises a pharmaceutically acceptable carrier or diluent and a conjugated compound that comprises a GCC binding moiety and an active moiety wherein the active moiety is a radioactive. In some embodiments of the present invention, the pharmaceutical composition comprises a pharmaceutically acceptable carrier or diluent and a conjugated compound that comprises a GCC binding moiety and an active moiety wherein the active moiety is a radioactive and the GCC binding moiety is an antibody. In some embodiments of the present invention, the pharmaceutical composition comprises a pharmaceutically acceptable carrier or diluent and a conjugated compound that comprises a GCC binding-moiety and an active moiety wherein the active moiety is a radioactive agent selected from the group consisting of: $^{47}$Sc, $^{67}$Cu, $^{90}$Y, $^{109}$Pd, $^{123}$I, $^{125}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, all beta negative and/or auger emitters. The individual being treated may be diagnosed as having metastasized cancer or may be diagnosed as having localized cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on primary and/or metastatic stomach or esophageal cancer cells without causing lethal side effects on the individual. The composition may be injected intratumorally into primary tumors.

One aspect of the present invention relates to a method of detecting primary and/or metastatic stomach or esophageal cancer cells in an individual suspected of suffering from primary or metastasized stomach or esophageal cancer by radioimaging. Individuals may be suspected of having primary stomach or esophageal tumors which diagnosis can be confirmed by administering to the individual, an imaging agent which binds to GCC. Tumors can be imaged by detecting localization at the stomach or esophagus. Individuals may be diagnosed as suffering from metastasized stomach or esophageal cancer and the metastasized stomach or esophageal cancer cells may be detected by administering to the individual, preferably by intravenous administration, a pharmaceutical composition that comprises a pharmaceutically acceptable carrier or diluent and a conjugated compound that comprises a GCC binding moiety and an active moiety wherein the active moiety is a radioactive and detecting the presence of a localized accumulation or aggregation of radioactivity, indicating the presence of cells with GCC. In some embodiments of the present invention, the pharmaceutical composition comprises a pharmaceutically acceptable carrier or diluent and a conjugated compound that comprises a GCC binding moiety and an active moiety wherein the active moiety is a radioactive and the GCC binding moiety is an antibody. In some embodiments of the present invention, the pharmaceutical composition comprises a pharmaceutically acceptable carrier or diluent and a conjugated compound that comprises an GCC binding moiety and an active moiety wherein the active moiety is a radioactive agent selected from the group consisting of: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{123}$I, $^{125}$I, $^{127}$Cs, $^{129}$Cs, $^{131}$I, $^{132}$I, $^{197}$Hg, $^{203}$Pb and $^{208}$Bi. The individual being treated may be diagnosed as having metastasizing stomach or esophageal cancer or may be diagnosed as having localized stomach or esophageal cancer and may undergo the treatment proactively in the event that there is some metastasis as yet undetected. The pharmaceutical composition contains a diagnostically effective amount of the conjugated composition. A diagnostically effective amount is an amount which can be detected at a site in the body where cells with GCC are located without causing lethal side effects on the individual.

Photodyasmic Imaging and Therapy

According to some embodiments of the invention, GCC binding moieties are conjugates to photoactivated imaging agents or therapeutics. Maier A. et al. Lasers in Surgery and Medicine 26:461-466 (2000) which is incorporated herein by reference disclose an example of photodynamic therapy. QLT, Inc (Vancouver, BC) commercially distribute photosensitive active agents which can be linked to GCC ligands. Such conjugated compounds can be used in photodynamic therapeutic and imaging protocols to activate the GCC-bound conjugated agents which are thus targeted to tumor cells. In some embodiments, the conjugated compounds are applied as an intraoperative spray which is subsequently exposed to light to activate compounds bound to cells that express GCC.

In some embodiments, the photodynamic agent is fluorophore or porphyrins. Examples of porphyrin include: hematoporphyrin derivative (HPD) and porfimer sodium (Photofrin®). A second generation photosensitizers is BPD verteporfin. In some embodiments the fluorophore is tetramethylrotamine. Lasers are generally the primary light source used to activate porphyrins. Light Emitting Diodes (LEDs) and florescent light sources may also be used in some applications.

In some embodiments, the photodynamic agent is linked to GCC at the GCC N-terminus.

In addition to an intraoperative spray, conjugated compounds may be delivered intrathecally, intraventrically, stereotactically, intrahepatically such as via the portal vein, by inhalation, and intrapleurally.

Drug Delivery Targeted to Stomach or Esophageal Cancer Cells Generally

Another aspect of the invention relates to unconjugated and conjugated compositions which comprise a OGCC ligand used to deliver therapeutic agents to cells that comprise a GCC such as primary and/or metastatic stomach or esophageal cancer cells. In some embodiments, the agent is a drug or toxin such as: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, *Pseudomonas* exotoxin, diphtheria toxin, *Clostridium pefringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. Genetic material is delivered to cancer cells to produce an antigen that can be targeted by the immune system or to produce a protein which kills the cell or inhibits its proliferation. In some embodiments, the GCC ligand is used to deliver nucleic acids that encode nucleic acid molecules which replace defective endogenous genes or which encode therapeutic proteins. In some embodiments, the compositions are used in gene therapy protocols to deliver to individuals, genetic material needed and/or desired to make up for a genetic deficiency.

In some embodiments, the GCC ligand is combined with or incorporated into a delivery vehicle thereby converting the delivery vehicle into a specifically targeted delivery vehicle. For example, a GCC binding peptide may be integrated into the outer portion of a viral particle making such a virus a GCC-bearing cell specific virus. Similarly, the coat protein of a virus may be engineered such that it is produced as a fusion protein which includes an active GCC binding peptide that is exposed or otherwise accessible on the outside of the viral particle making such a virus a GCC-bearing cell-specific virus. In some embodiments, a GCC ligand may be integrated or otherwise incorporated into the liposomes wherein the GCC ligand is exposed or otherwise accessible on the outside of the liposome making such liposomes specifically targeted to GCC-bearing cells.

The active agent in the conjugated or unconjugated compositions according to this aspect of the invention is a drug, toxin or nucleic acid molecule. The nucleic acid may be RNA or preferably DNA. In some embodiments, the nucleic acid molecule is an antisense molecule or encodes an antisense sequence whose presence in the cell inhibits production of an undesirable protein. In some embodiments, the nucleic acid molecule encodes a ribozyme whose presence in the cell inhibits production of an undesirable protein. In some embodiments, the nucleic acid molecule encodes a protein or peptide that is desirably produced in the cell. In some embodiments, the nucleic acid molecule encodes a functional copy of a gene that is defective in the targeted cell. The nucleic acid molecule is preferably operably linked to regulatory elements needed to express the coding sequence in the cell.

Liposonmes are small vesicles composed of lipids. Genetic constructs which encode proteins that are desired to be expressed in GCC-bearing cells are introduced into the center of these vesicles. The outer shell of these vesioles comprise an a GCC ligand. *Liposomes* Volumes 1, 2 and 3 CRC Press Inc. Boca Raton Fla., which is incorporated herein by reference, disclose preparation of liposome-encapsulated active agents which include antibodies in the outer shell. In the present invention, a GCC ligand such as for example an anti-GCC antibodies is associated with the in the outer shell. Unconjugated compositions which comprise a GCC ligand in the matrix of a liposome with an active agent inside include such compositions in which the GCC ligand is preferably an antibody.

In one embodiment, the delivery of normal copies of the p53 tumor suppressor gene to the cancer cells is accomplished using GCC ligand to target the gene therapeutic. Mutations of the p53 tumor suppressor gene appears to play a prominent role in the development of many cancers. One approach to combating this disease is the delivery of normal copies of this gene to the cancer cells expressing mutant forms of this gene. Genetic constructs that comprise normal p53 tumor suppressor genes are incorporated into liposomes that comprise a GCC ligand. The composition is delivered to the tumor. GCC ligands specifically target and direct the liposomes containing the normal gene to correct the lesion created by mutation of p53 suppressor gene. Preparation of genetic constructs is with the skill of those having ordinary skill in the art. The present invention allows such construct to be specifically targeted by using the GCC ligands of the present invention. The compositions of the invention include a GCC ligand such as an anti-GCC antibody associated with a delivery vehicle and a gene construct which comprises a coding sequence for a protein whose production is desired in the cells of the intestinal tract linked to necessary regulatory sequences for expression in the cells. For uptake by cells of the intestinal tract, the compositions are administered orally or by enema whereby they enter the intestinal tract and contact cells which comprise GCC. The delivery vehicles associate with the GCC by virtue of the GCC ligand and the vehicle is internalized into the cell or the active agent/genetic construct is otherwise taken up by the cell. Once internalized, the construct can provide a therapeutic effect on the individual.

Antisense

The present invention provides compositions, kits and methods which are useful to prevent and treat stomach or esophageal cancer cells by providing the means to specifically deliver antisense compounds to stomach or esophageal cancer cells and thereby stop expression of genes in such cells in which undesirable gene expression is taking place without negatively effecting cells in which no such expression occurs.

The conjugated compositions of the present invention are useful for targeting cells that express GCC including stomach or esophageal cancer cells. The conjugated compositions will not bind to non-colorectal derived cells. Non-colorectal cells, lacking GCC, do not take up the conjugated compositions. Normal colorectal cells do have GCC and will take up the compositions. The present invention provides compositions and methods of delivering antisense compositions to stomach or esophageal cancer cells.

The present invention provides a cell specific approach in which only normal and cancerous colorectal cells and primary and/or metastatic stomach or esophageal cancer cells are exposed to the active portion of the compound and only those cells are effected by the conjugated compound. The GCC binding moiety binds to normal and cancerous colorectal cells and primary and/or metastatic stomach or esophageal cancer cells. Upon binding to these cells, the conjugated compound is internalized and the delivery of the conjugated compound including the antisense portion of the molecule is effected. The presence of the conjugated compound in normal colorectal cells has no effect on such cells because the cancer-associated gene for which the antisense molecule that makes up the active moiety of the conjugated compound is complementary is not being expressed. However, in colorectal cancer cells, the cancer gene for which the antisense molecule that makes up the active moiety of the conjugated compound is complementary is being expressed. The presence of the conjugated compound in colorectal cancer cells serves to inhibit or prevent transcription or translation of the cancer gene and thereby reduce or eliminate the transformed phenotype.

The invention can be used to combat primary and/or metastasized colorectal, stomach or esophageal cancer as well as to prevent the emergence of the transformed phenotype in normal colon cells. Thus the invention can be used therapeutically as well as prophylactically.

One having ordinary skill in the art can readily identify individuals suspected of suffering from stomach or esophageal cancer. In those individuals diagnosed with stomach or esophageal cancer, it is standard therapy to suspect metastasis and aggressively attempt to eradicate metastasized cells. The present invention provides pharmaceutical compositions and methods for specifically targeting and eliminating primary and/or metastatic stomach or esophageal cancer cells. Further, the present invention provides pharmaceutical compositions that comprise therapeutics and methods for specifically eliminating primary and/or metastatic stomach or esophageal cancer cells.

The present invention relies upon the use of a GCC binding moiety in a conjugated composition. The GCC product binding moiety is essentially a portion of the conjugated composition which acts as a ligand to the GCC and thus specifically binds to these receptors. The conjugated composition also includes an active moiety which is associated with the GCC binding moiety; the active moiety being an antisense composition useful to inhibit or prevent transcription or translation of expression of genes whose expression is associated with cancer.

According to the present invention, the active moiety is an antisense composition. In particular, the antisense molecule that makes up the active moiety of a conjugated compound hybridizes to DNA or RNA in a stomach or esophageal cancer cell and inhibits and/or prevents transcription or translation of the DNA or RNA from taking place. The antisense compositions may be a nucleic acid molecule, a derivative or an analogs thereof. The chemical nature of the antisense composition may be that of a nucleic acid molecule or a modified nucleic acid molecule or a non-nucleic acid molecule which possess functional groups that mimic a DNA or RNA molecule that is complementary to the DNA or RNA molecule whose expression is to be inhibited or otherwise prevented. Antisense compositions inhibit or prevent transcription or translation of genes whose expression is linked to stomach or esophageal cancer, i.e. cancer associated genes.

Point mutations insertions, and deletions in K-ras and H-ras have been identified in many tumors. Complex characteristics of the alterations of oncogenes HER-2/ERBB-2, HER-1/ERBB-1, HRAS-1, C-MYC and anti-oncogenes p53, RB 1.

Chemical carcinogenesis in a rat model demonstrated point mutations in fos, an oncogene which mediates transcriptional regulation and proliferation. See: Alexander, R J, et al. Oncogene alterations in rat colon tumors induced by N-methyl-N-nitrosourea. *American Journal of the Medical Sciences*. 303(1):16-24, 1992, January which is hereby incorporated herein by reference including all references cited therein which are also hereby incorporated herein by reference.

Chemical carcinogenesis in a rat model demonstrated point mutations in the oncogene abl. See: Alexander, R J, et al. Oncogene alterations in rat colon tumors induced by N-methyl-N-nitrosourea. *American Journal of the Medical Sciences.* 303(1): 16-24, 1992, January.

MYC is an oncogene that plays a role in regulating transcription and proliferation. A 15-base antisense oligonucleotide to myc complementary to the translation initiation region of exon II was incubated with colorectal cancer cells. This antisense molecule inhibited proliferation of colorectal cancer cells in a dos-dependent fashion. Interestingly, the uptake of this oligonucleotide was low (0.7%). Also, transfer of a normal chromosome 5 to colorectal cancer cells resulted in the regulation of myc expression and loss of proliferation. These data suggest that a tumor suppressor gene important in the regulation of myc is contained on this chromosome.

A novel protein tyrosine phosphatase, G1, has been identified. Examination of the mRNA encoding this protein in colorectal tumor cells revealed that it undergoes point mutations and deletions in these cells and may play a role in proliferation characteristic of these cells. Takekawa, M. et al., Chromosomal localization of the protein tyrosine phosphatase G1 gene and characterization of the aberrant transcripts in human colon cancer cells. *FEBS Leters.* 339(3): 2224, 1994 Feb. 21, which is hereby incorporated herein by reference including all references cited therein which are also hereby incorporated herein by reference.

Gastrin regulates colon cancer cell growth through a cyclic AMP-dependent mechanism mediated by PKA. Antisense oligodeoxynucleotides to the regulatory subunit of a specific class of PKA inhibited the growth-promoting effects of cyclic AMP in colon carcinoma cells. See: Bold, R J, et al. Experimental gene therapy of human colon cancer. *Surgery.* 116(2):189-95; discussion 195-6, 1994 August and Yokozaki, H., et al. An antisense oligodeoxynucleotide that depletes RI alpha subunit of cyclic AMP-dependent protein kinase induces growth inhibition in human cancer cells. *Cancer Research.* 53(4):868-72, 1993 Feb. 15, which are both hereby incorporated herein by reference including all references cited therein which are also hereby incorporated herein by reference.

CRIPTO is an epidermal growth factor-related gene expressed in a majority of colorectal cancer tumors. Antisense phosphorothioate oligodeoxynucleotides to the 5'-end of CRIPTO mRNA significantly reduced CRIPTO expression and inhibited colorectal tumor cell growth in vitro and in vivo. Ciardiello, F. et al. Inhibition of CRIPTO expression and tumorigenicity in human colon cancer cells by antisense RNA and oligodeoxynucleotides. *Oncogene.* 9(1):291-8, 1994 January which are both hereby incorporated herein by reference including all references cited therein which are also hereby incorporated herein by reference.

Many carcinoma cells secrete transforming growth factor alpha. A 23 nucleotide antisense oligonucleotide to TGF alpha mRNA inhibited both DNA synthesis an proliferation of colorectal cancer cells. Sizeland, A M, Burgess, A W. Antisense transforming growth factor alpha oligonucleotides inhibit autocrine stimulated proliferation of a colon carcinoma cell line. *Molecular Biology of the Cell.* 3(11): 1235-43, 1992 November which is hereby incorporated herein by reference including all references cited therein which are also hereby incorporated herein by reference.

Antisense compositions including oligonucleotides, derivatives and analogs thereof, conjugation protocols, and antisense strategies for inhibition of transcription and translation are generally described in: *Antisense Research and Applications*, Crooke, S. and B. Lebleu, eds. CRC Press, Inc. Boca Raton Fla. 1993; *Nucleic Acids in Chemistry and Biology* Blackburn, G. and M. J. Gait, eds. IRL Press at Oxford University Press, Inc. New York 1990; and *Oligonucleotides and Analogues: A Practical Approach* Eckstein, F. ed., IRL Press at Oxford University Press, Inc. New York 1991; which are each hereby incorporated herein by reference including all references cited therein which are hereby incorporated herein by reference.

The antisense molecules of the present invention comprise a sequence complementary to a fragment of a colorectal cancer gene. See Ullrich et al., *EMBO J.,* 1986, 5:2503, which is hereby incorporated herein by reference.

Antisense compositions which can make up an active moiety in conjugated compounds of the invention include oligonucleotides formed of homopyrimidines can recognize local stretches of homopwines in the DNA double helix and bind to them in the major groove to form a triple helix. See: Helen, C and Toulme, J J. Specific regulation of gene expression by antisense, sense, and antigene nucleic acids. *Biochem. Biophys Acta,* 1049:99-125, 1990 which is hereby incorporated herein by reference including all references cited therein which are hereby incorporated herein by reference. Formation of the triple helix would interrupt the ability of the specific gene to undergo transcription by RNA polymerase. Triple helix formation using myc-specific oligonucleotides has been observed. See: Cooney, M, et al. *Science* 241:456-459 which is hereby incorporated herein by reference including all references cited therein which are hereby incorporated herein by reference.

Antisense oligonucleotides of DNA or RNA complementary to sequences at the boundary between introns and exons can be employed to prevent the maturation of newly-generated nuclear RNA transcripts of specific genes into mRNA for transcription.

Antisense RNA complimentary to specific genes can hybridize with the mRNA for tat gene and prevent its translation. Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Antisense sequences of DNA or RNA can be delivered to cells. Several chemical modifications have been developed to prolong the stability and improve the function of these molecules without interfering in their ability to recognize specific sequences. These include increasing their resistance to degradation by DNases, including phosphotriesters, methyiphosphonates, phosphorothioates, alpha-anomers, increasing their affinity for their target by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Conjugated compositions of the invention provide a specific and effective means for terminating the expression of genes which cause neoplastic transformation. GCC undergo ligand-induced endocytosis and can deliver conjugated compounds to the cytoplasm of cells.

GCC-binding moieties are conjugated directly to antisense compositions such as nucleic acids which are active in inducing a response. For example, antisense oligonucleotides to MYC are conjugated directly to an anti-GCC antibody. This has been performed employing peptides that bind to the CD4 receptor. See: Cohen, J S, ed. *Oligodeoxynucleotide: Antisense Inhibitors of Gene Expression. Topics in Molecular and Structural Biology*. CRC Press, Inc., Boca Raton, 1989, which is hereby incorporated herein by reference including all references cited therein which are hereby incorporated herein by reference. The precise backbone and its synthesis is not specified and can be selected from well-established techniques. Synthesis would involve either chemical conjugation or direct synthesis of the chimeric molecule by solid phase synthesis employing FMOC chemistry. See: Haralambidis, 1, et al. (1987) *Tetrahedron Lett.* 28:5199-5202, which is hereby incorporated herein by reference including all references cited therein which are hereby incorporated herein by reference. Alternatively, the peptide-nucleic acid conjugate may be synthesized directly by solid phase synthesis as a peptide-peptide nucleic acid chimera by solid phase synthesis. Nielsen, P E, et al. (1994) Sequence-specific transcription arrest by peptide nucleic acid bound to the DNA template strand. *Gene* 149:139-145, which is hereby incorporated herein by reference including all references cited therein which are hereby incorporated herein by reference.

In some embodiments, polylysine can be complexed to conjugated compositions of the invention in a non-covalent fashion to nucleic acids and used to enhance delivery of these molecules to the cytoplasm of cells. In addition, peptides and proteins can be conjugated to polylysine in a covalent fashion and this conjugate complexed with nucleic acids in a non-covalent fashion to further enhance the specificity and efficiency of uptake of the nucleic acids into cells. Thus, GCC ligand is conjugated chemically to polylysine by established techniques. The polylysine-GCC-1 translation product ligand conjugate may be complexed with nucleic acids of choice. Thus, polylysine-orosomucoid conjugates were employed to specifically plasmids containing genes to be expressed to hepatoma cells expressing the orosomucoid receptor. This approach can be used to delivery whole genes, or oligonucleotides. Thus, it has the potential to terminate the expression of an undesired gene (eg. MYC, ras) or replace the function of a lost or deleted gene (eg. hMSH2, hMLHI, hPMS1, and hPMS2).

According to a preferred embodiment, Myc serves as a gene whose expression is inhibited by an antisense molecule within a conjugated composition. GCC binding moieties are used to deliver a IS-based antisense oligonucleotide to myc complementary to the translation initiation region of exon II. The 15-base antisense oligonucleotide to MYC is synthesized as reported in Collins, J F, Herman, P, Schuch, C, Bagby G C, Jr. *Journal of Clinical Investigation.* 89(5): 1523-7, 1992 May. In some embodiments, the conjugated composition is conjugated to polylysine as reported previously. Wu, G Y, and Wu, C H. (1988) Evidence for ed gene delivery to Hep G2 hepatoma cells in vitro. *Biochem.* 27:887-892 which is incorporated herein by reference.

Conjugated compositions may be synthesized as a chimeric molecule directly by solid phase synthesis. pmolar to nanomolar concentrations for this conjugate suppress MYC synthesis in colorectal cancer cells in vitro.

Antisense molecules are preferably hybridize to, i.e. are complementary to, a nucleotide sequence that is 5-50 nucleotides in length, more preferably 5-25 nucleotides and in some embodiments 10-15 nucleotides.

In addition, mismatches within the sequences identified above, which achieve the methods of the invention, such that the mismatched sequences are substantially complementary to the cancer gene sequences are also considered within the scope of the disclosure. Mismatches which permit substantial complementarity to the cancer gene sequences will be known to those of skill in the art once armed with the present disclosure. The oligos may also be unmodified or modified.

Therapeutic compositions and methods may be used to combat stomach or esophageal cancer in cases where the cancer is localized and/or metastasized. Individuals are administered a therapeutically effective amount of conjugated compound. A therapeutically effective amount is an amount which is effective to cause a cytotoxic or cytostatic effect on cancer cells without causing lethal side effects on the individual. An individual who has been administered a therapeutically effective amount of a conjugated composition has a increased chance of eliminating stomach or esophageal cancer as compared to the risk had the individual not received the therapeutically effective amount.

To treat localized stomach or esophageal cancer, a therapeutically effective amount of a conjugated compound is administered such that it will come into contact with the localized tumor. Thus, the conjugated compound may be administered orally or intratumorally. Oral and rectal formulation are taught in Remington's Pharmaceutical Sciences, 18th Edition, 1990, Mack Publishing Co., Easton Pa. which is incorporated herein by reference.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The present invention is directed to a method of delivering antisense compounds to normal and cancerous colorectal cells and to stomach or esophageal cancer cells and inhibiting expression of cancer genes in mammals. The methods comprise administering to a mammal an effective amount of a conjugated composition which comprises a GCC binding moiety conjugated to an antisense oligonucleotide having a sequence which is complementary to a region of DNA or mRNA of a cancer gene.

The conjugated compounds may be administering to mammals in a mixture with a pharmaceutically-acceptable carrier, selected with regard to the intended route of administration and the standard pharmaceutical practice. Dosages will be set with regard to weight, and clinical condition of the patient. The conjugated compositions of the present invention will be administered for a time sufficient for the mammals to be free of undifferentiated cells and/or cells having an abnormal phenotype. In therapeutic methods treatment extends for a time sufficient to inhibit transformed cells from proliferating and conjugated compositions may be administered in conjunction with other chemotherapeutic agents to manage and combat the patient's cancer.

The conjugated compounds of the invention may be employed in the method of the invention singly or in combination with other compounds. The amount to be administered will also depend on such factors as the age, weight, and clinical condition of the patient See Gennaro, Alfonso, ed., *Remington's Pharmaceutical Sciences,* 18th Edition, 1990, Mack Publishing Co., Easton Pa.

Therapeutic and Prophylactic Vaccines

The invention relates to prophylactic and therapeutic vaccines for protecting individuals against primary and/or metastatic stomach or esophageal cancer cells and for treating individuals who are suffering from primary and/or metastatic stomach or esophageal cancer cells.

According to the present invention, GCC serves as targets against which a protective and therapeutic immune response can be induced. Specifically, vaccines are provided which induce an immune response against GCC. The vaccines of the invention include, but are not limited to, the following vaccine technologies:

1) DNA vaccines, i.e. vaccines in which DNA that encodes at least an epitope from an GCC is administered to an individual's cells where the epitope is expressed and serves as a target for an immune response;

2) infectious vector mediated vaccines such as recombinant adenovirus, vaccinia, *Salmonella*, and BCG wherein the vector carries genetic information that encodes at least an epitope from an GCC protein such that when the infectious vector is administered to an individual, the epitope is expressed and serves as a target for an immune response;

3) killed or inactivated vaccines which a) comprise either killed cells or inactivated viral particles that display at least an epitope from an GCC protein and b) when administered to an individual serves as a target for an immune response;

4) haptenized killed or inactivated vaccines which a) comprise either killed cells or inactivated viral particles that display at least an epitope from an GCC protein, b) are haptenized to be more immunogenic and c) when administered to an individual serves as a target for an immune response;

5) subunit vaccines which are vaccines that include protein molecules that include at least an epitope from an GCC protein; and 6) haptenized subunit vaccines which are vaccines that a) include protein molecules that include at least an epitope from an GCC protein and b) are haptenized to be more immunogenic.

The present invention relates to administering to an individual a protein or nucleic acid molecule that comprises or encodes, respectively, an immunogenic epitope against which an therapeutic and prophylactic immune response can be induced. Such epitopes are generally at least 6-8 amino acids in length. The vaccines of the invention therefore comprise proteins which are at least, or nucleic acids which encode at least, 6-8 amino acids in length from GCC protein. The vaccines of the invention may comprise proteins which are at least, or nucleic acids which encode at least 10 to about 1000 amino acids in length. The vaccines of the invention may comprise proteins which are at least, or nucleic acids which encode at least, about 25 to about 500 amino acids in length. The vaccines of the invention may comprise proteins which are at least, or nucleic acids which encode at least, about 50 to about 400 amino acids in length. The vaccines of the invention may comprise proteins which are at least, or nucleic acids which encode at least, about 100 to about 300 amino acids in length.

The present invention relates to compositions for and methods of treating individuals who are known to have primary and/or metastatic stomach or esophageal cancer cells. Primary and/or metastatic stomach or esophageal cancer may be diagnosed by those having ordinary skill in the art using the methods described herein or art accepted clinical and laboratory pathology protocols. The present invention provides an immunotherapeutic vaccine useful to treat individuals who have been diagnosed as suffering from primary and/or metastatic stomach or esophageal cancer. The immunotherapeutic vaccines of the present invention may be administered in combination with other therapies.

The present invention relates to compositions for and methods of preventing primary and/or metastatic stomach or esophageal cancer in individual is suspected of being susceptible to stomach or esophageal cancer. Such individuals include those whose family medical history indicates above average incidence of stomach or esophageal cancer among family members and/or those who have already developed stomach or esophageal cancer and have been effectively treated who therefore face a risk of relapse and recurrence. Such individuals include those which have been diagnosed as having stomach or esophageal cancer including localized only or localized and metastasized stomach or esophageal cancer which has been resected or otherwise treated. The vaccines of the present invention may be to susceptible individuals prophylactically to prevent and combat primary and metastatic stomach or esophageal cancer.

The invention relates to compositions which are the active components of such vaccines or required to make the active components, to methods of making such compositions including the active components, and to methods of making and using vaccines.

The amino acid and nucleotide sequences of the GCC is set forth as SEQ ID NO:1.

The present invention relates to recombinant vectors, including expression vectors, that comprise the GCC gene transcript or a fragment thereof. The present invention relates to recombinant vectors, including expression vectors that comprise nucleotide sequences that encode a GCC protein or a functional fragment thereof.

The present invention relates to host cells which comprise such vectors and to methods of making GCC protein using such recombinant cells.

The present invention relates to the isolated GCC gene transcript and to the isolated GCC proteins and to isolated antibodies specific for such protein and to hybridomas which produce such antibodies.

The present invention relates to the isolated GCC and functional fragments thereof. Accordingly, some aspects of the invention relate to isolated proteins that comprise at least one epitope of an GCC.

Some aspects of the invention relate to the above described isolated proteins which are haptenized to render them more immunogenic. That is, some aspects of the invention relate to haptenized proteins that comprise at least one GCC epitope.

Accordingly, some aspects of the invention relate to isolated nucleic acid molecules that encode proteins that comprise at least one GCC epitope.

Naked DNA vaccines are described in PCT/US90/01515, which is incorporated herein by reference. Others teach the use of liposome mediated DNA transfer, DNA delivery using microprojectiles (U.S. Pat. No. 4,945,050 issued Jul. 31, 1990 to Sanford et al., which is incorporated herein by reference), and DNA delivery using electroporation. In each case, the DNA may be plasmid DNA that is produced in bacteria, isolated and administered to the animal to be treated. The plasmid DNA molecules are taken up by the cells of the animal where the sequences that encode the protein of interest are expressed. The protein thus produced provides a therapeutic or prophylactic effect on the animal.

The use of vectors including viral vectors and other means of delivering nucleic acid molecules to cells of an individual in order to produce a therapeutic and/or prophylactic immunological effect on the individual are similarly well known. Recombinant vaccines that employ vaccinia vectors are, for example, disclosed in U.S. Pat. No. 5,017,487 issued May 21, 1991 to Stunnenberg et al. which is incorporated herein by reference.

In some cases, tumor cells from the patient are killed or inactivated and administered as a vaccine product. Berd et al. May 1986 *Cancer Research* 46:2572-2577 and Berd et al. May 1991 *Cancer Research* 51:2731-2734, which are incorporated herein by reference, describes the preparation and use of tumor cell based vaccine products. According to some aspects of the present invention, the methods and techniques described in Berd et al. are adapted by using stomach or esophageal cancer cells instead of melanoma cells.

The manufacture and use of isolated translation products and fragments thereof useful for example as laboratory reagents or components of subunit vaccines are well known. One having ordinary skill in the art can isolate the GCC gene transcript or the specific portion thereof that encodes GCC or a fragment thereof. Once isolated, the nucleic acid molecule can be inserted it into an expression vector using standard techniques and readily available starting materials.

The recombinant expression vector that comprises a nucleotide sequence that encodes the nucleic acid molecule that encodes GCC or a fragment thereof or a protein that comprises the GCC or a fragment thereof. The recombinant expression vectors of the invention are useful for transforming hosts to prepare recombinant expression systems for preparing the isolated proteins of the invention.

The present invention relates to a host cell that comprises the recombinant expression vector that includes a nucleotide sequence that encodes GCC protein or a fragment thereof or an GCC or a fragment thereof. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the proteins of the invention. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes GCC or a fragment thereof or a protein that comprises GCC or a fragment thereof operably linked to a mammary cell specific promoter whereby the coding sequence is only expressed in mammary cells and the recombinant protein so expressed is recovered from the animal's milk.

In some embodiments, for example, one having ordinary skill in the art can, using well known techniques, insert such DNA molecules into a commercially available expression vector for use in well known expression systems such as those described herein.

The expression vector including the DNA that encodes a GCC or a functional fragment thereof or a protein that comprises a GCC or a functional fragment thereof is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. The methods of purifying the GCC or a fragment thereof or a protein that comprises the same using antibodies which specifically bind to the protein are well known. Antibodies which specifically bind to a particular protein may be used to purify the protein from natural sources using well known techniques and readily available starting materials. Such antibodies may also be used to purify the protein from material present when producing the protein by recombinant DNA methodology. The present invention relates to antibodies that bind to an epitope which is present on one or more GCC-1 translation products or a fragment thereof or a protein that comprises the same. Antibodies that bind to an epitope which is present on the GCC are useful to isolate and purify the protein from both natural sources or recombinant expression systems using well known techniques such as affinity chromatography. Immunoaffinity techniques generally are described in Waldman et al. 1991 *Methods of Enzymol.* 195:391-396, which is incorporated herein by reference. Antibodies are useful to detect the presence of such protein in a sample and to determine if cells are expressing the protein. The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference.

In some embodiments of the invention, transgenic non-human animals are generated. The transgenic animals according to the invention contain nucleotides that encode GCC or a fragment therefor a protein that comprises the same under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce GCC or a fragment thereof or a protein that comprises the same. Preferred animals are goats and rodents, particularly rats and mice.

In addition to producing these proteins by recombinant techniques, automated peptide synthesizers may also be employed to produce GCC or a fragment thereof or a fragment thereof or a protein that comprises the same. Such techniques are well known to those having ordinary skill in the art and are useful if derivatives which have substitutions not provided for in DNA-encoded protein production.

In some embodiments, the protein that makes up a subunit vaccine or the cells or particles of a killed or inactivated vaccine may be haptenized to increase immunogenicity. In some cases, the haptenization is the conjugation of a larger molecular structure to GCC or a fragment thereof or a protein that comprises the same. In some cases, tumor cells from the patient are killed and haptenized as a means to make an effective vaccine product. In cases in which other cells, such as bacteria or eukaryotic cells which are provided with the genetic information to make and display a GCC or a fragment thereof or a protein that comprises the same, are killed and used as the active vaccine component, such cells are haptenized to increase immunogenicity. Haptenization is well known and can be readily performed.

Methods of haptenizing cells generally and tumor cells in particular are described in Berd et al. May 1986 *Cancer Research* 46:2572-2577 and Berd et al. May 1991 *Cancer Research* 51:2731-2734, which are incorporated herein by reference. Additional haptenization protocols are disclosed in Miller et al. 1976 *J. Immunol.* 117(5:1):1591-1526.

Haptenization compositions and methods which may be adapted to be used to prepare haptenized GCC immunogens according to the present invention include those described in the following U.S. patents which are each incorporated herein by reference: U.S. Pat. No. 5,037,645 issued Aug. 6, 1991 to Strahilevitz; U.S. Pat. No. 5,112,606 issued May 12, 1992 to Shiosaka et al.; U.S. Pat. No. 4,526,716 issued Jul. 2, 1985 to Stevens; U.S. Pat. No. 4,329,281 issued May 11, 1982 to Christenson et al.; and U.S. Pat. No. 4,022,878 issued May 10, 1977 to Gross. Peptide vaccines and methods of enhancing immunogenicity of peptides which may be adapted to modify GCC immunogens of the invention are also described in Francis et al. 1989 *Methods of Enzymol.* 178:659-676, which is incorporated herein by reference. Sad et al. 1992 *Immunolology* 76:599-603, which is incorporated herein by reference, teaches methods of making immunotherapeutic vaccines by conjugating gonadotropin releasing hormone to diphtheria toxoid. GCC immunogens may be similarly conjugated to produce an immunotherapeutic vaccine of the present invention. MacLean et al. 1993 *Cancer Immunol. Immunother.* 36:215-222, which is incorporated herein by reference, describes conjugation methodologies for producing immunotherapeutic vaccines which may be adaptable to produce an immunotherapeutic vaccine of the present invention. The hapten is keyhole limpet hemocyanin which may be conjugated to a GCC immunogen.

Vaccines according to some aspects of the invention comprise a pharmaceutically acceptable carrier in combination with a GCC immunogen. Pharmaceutical formulations are well known and pharmaceutical compositions comprising such proteins may be routinely formulated by one having ordinary skill in the art. Suitable pharmaceutical carriers are described in *Remington's Pharmaceutical Sciences*, A. Osol, a standard reference text in this field, which is incorporated herein by reference. The present invention relates to an injectable pharmaceutical composition that comprises a pharmaceutically acceptable carrier and a GCC immunogen. The GCC immunogen is preferably sterile and combined with a sterile pharmaceutical carrier.

In some embodiments, for example, GCC or a fragment thereof or a fragment thereof or a protein that comprises the same can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise the GCC immunogen in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

The vaccines of the present invention may be administered by any means that enables the immunogenic agent to be presented to the body's immune system for recognition and induction of an immunogenic response. Pharmaceutical compositions may be administered parenterally, i.e., intravenous, subcutaneous, intramuscular.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. An amount of immunogen is delivered to induce a protective or therapeutically effective immune response. Those having ordinary skill in the art can readily determine the range and optimal dosage by routine methods.

The following examples are illustrative but are not meant to be limiting of the present invention.

EXAMPLES

As stated above, a GCC binding moiety is a GCC ligand that may be an antibody, a protein, a polypeptide, a peptide or a non-peptide. Peptides and non-peptide GCC ligands may be identified using well known technology.

Over the past 10 years, it has become recognized that the specific high-affinity interaction of a receptor and a ligand, for example a GCC and an anti-GCC antibody, has its basis in the 3-dimensional conformational space of the ligand and the complimentary 3-dimensional configuration of the region of the molecule involved in ligand binding. In addition, it has become recognized that various arrays of naturally-occurring amino acids, non-natural amino acids, and organic molecules can be organized in configurations that are unrelated to the natural ligands in their linear structure, but resemble the 3-dimensional structure of the natural ligands in conformational space and, thus, are recognized by receptors with high affinity and specificity. Furthermore, techniques have been described in the literature that permit one of ordinary skill in the art to generate large libraries of these arrays of natural amino acids, non-natural amino acids and organic compounds to prospectively identify individual compounds that interact with receptors with high affinity and specificity which are unrelated to the native ligand of that receptor. Thus, it is a relatively straightforward task for one of ordinary skill in the art to identify arrays of naturally occurring amino acids, non-natural amino acids, or organic compounds which can bind specifically and tightly to the GCC, which bear no structural relationship to an anti-GCC antibody.

To identify GCC ligands that are peptides, those having ordinary skill in the art can use any of the well known methodologies for screening random peptide libraries in order to identify peptides which bind to the GCC. In the most basic of methodologies, the peptides which bind to the target are isolated and sequenced. In some methodologies, each random peptide is linked to a nucleic acid molecule which includes the coding sequence for that particular random peptide. The random peptides, each with an attached coding sequence, are contacted with a GCC and the peptides which are unbound to the GCC are removed. The nucleic acid molecule which includes the coding sequence of the peptide that binds to the GCC can then be used to determine the amino acid sequence of the peptide as well as produce large quantities of the peptide. It is also possible to produce peptide libraries on solid supports where the spatial location on the support corresponds to a specific synthesis and therefore specific peptide. Such methods often use photolithography-like steps to create diverse peptide libraries on solid supports in which the spatial address on the support allows for the determination of the sequence.

The production of organic compound libraries on solid supports may also be used to produce combinatorial libraries of non-peptide compounds such as oligonucleotides and sugars, for example. As in the case of peptide libraries on solid supports, the spatial location on the support corresponds to a specific synthesis and therefore specific compound. Such methods often use photolithography-like steps to create diverse compound libraries on solid supports in which the spatial address on the support allows for the determination of the synthesis scheme which produced the compound. Once the synthesis scheme is identified, the structure of the compound can become known.

Gallop et al. 1994 *J. Medicinal Chemistry* 37:1233, which is incorporated herein by reference, provides a review of several of the various methodologies of screening random peptide libraries and identifying peptides from such libraries which bind to target proteins. Following these teachings, GCC specific ligands that are peptides and that are useful as GCC specific binding moieties may be identified by those having ordinary skill in the art.

Peptides and proteins displayed on phage particles are described in Gallop et al. Supra. Random arrays of nucleic acids can be inserted into genes encoding surface proteins of bacteriophage which are employed to infect bacteria, yielding phage expressing the peptides encoded by the random array of nucleotides on their surface. These phage displaying the peptide can be employed to determine whether those peptides can bind to specific proteins, receptors, antibodies, etc. The identity of the peptide can be determined by sequencing the recombinant DNA from the phage expressing the peptide. This approach has the potential to yield vast arrays of peptides in a library (up to $10^9$ unique peptides). This technique has been employed to identify novel binding peptides to the fibrinogen receptor on platelets, which bear no sequence homology to the natural occurring ligands of this receptor (Smith et al., 1993 *Gene* 128:37, which is incorporated herein by reference). Similarly, this technique has been applied to identify peptides which bind to the MHC class II receptor (Hammer et al., 1993 *Cell* 74:197, which is incorporated herein by reference) and the chaperonin receptor (Blond-Elguindi et al., 1993 *Cell* 75:717, which is incorporated herein by reference).

Peptides displayed on plasmids are described in Gallop et al. Supra. In this approach, the random oligonucleotides which encode the library of peptides can be expressed on a specific plasmid whose expression is under the control of a specific promoter, such as the lac operon. The peptides are expressed as fusion proteins coupled to the Lac I protein, under the control of the lac operon. The fusion protein specifically binds to the lac operator on the plasmid and so the random peptide is associated with the specific DNA element that encodes it. In this way, the sequence of the peptide can be deduced, by PCR of the DNA associated with the fusion protein. These proteins can be screened in solution phase to determine whether they bind to specific receptors. Employing this approach, novel substrates have been identified for specific enzymes (Schatz 1993).

A variation of the above technique, also described in Gallop et a. Supra, can be employed in which random oligonucleotides encoding peptide libraries on plasmids can be expressed in cell-free systems. In this approach, a molecular DNA library can be constructed containing the random array of oligonucleotides, which are then expressed in a bacterial in vitro transcription/translation system. The identity of the ligand is determined by purifying the complex of nascent chain peptidelpolysome containing the mRNA of interest on affinity resins composed of the receptor and then sequencing following amplification with RT-PCR. Employing this technique permits generation of large libraries (up to $10^{11}$ recombinants). Peptides which recognize antibodies specifically directed to dynorphin have been identified employing this technique (Cull et al., 1992 *Proc. Natl. Acad. Sci. USA* 89:1865, which is incorporated herein by reference).

Libraries of peptides can be generated for screening against a receptor by chemical synthesis. For example, simultaneous preparation of large numbers of diverse peptides have been generated employing the approach of multiple peptide synthesis as described in Gallop et al. Supra. In one application, random peptides are generated by standard solid-phase Merrifield synthesis on polyacrylamide microtiter plates (multipin synthesis) which are subsequently screened for their ability to compete with receptor binding in a standard competitive binding assay (Wang et al., 1993 *Bioorg. Med. Chem. Lett.* 3:447, which is incorporated herein by reference). Indeed, this approach has been employed to identify novel binding peptides to the substance P receptor (Wang et al. Supra). Similarly, peptide libraries can be constructed by multiple peptide synthesis employing the "tea bag" method in which bags of solid support resin are sequentially incubated with various amino acids to generate arrays of different peptides (Gallop et al. Supra). Employing this approach, peptides which bind to the integrin receptor (Ruggeri et al, 1986 *Proc. Natl. Acad Sci. USA* 83:5708, which is incorporated herein by reference) and the neuropeptide Y receptor (Beck-Sickinger et al., 1990 *Int. J. Peptide Protein Res.* 36:522, which is incorporated herein by reference) have been identified.

In general, the generation and utility of combinatorial libraries depend on (1) a method to generate diverse arrays of building blocks, (2) a method for identifying members of the array that yield the desired function, and (3) a method for deconvoluting the structure of that member. Several approaches to these constraints have been defined.

The following is a description of methods of library generation which can be used in procedures for identifying GCC ligands according to the invention.

Modifications of the above approaches can be employed to generate libraries of vast molecular diversity by connecting together members of a set of chemical building blocks, such as amino acids, in all possible combinations (Gallop er al. Supra) In one approach, mixtures of activated monomers are coupled to a growing chain of amino acids on a solid support at each cycle. This is a multivalent synthetic system.

Also, split synthesis involves incubating the growing chain in individual reactions containing only a single building block (Gallop el al. Supra). Following attachment, resin from all the reactions are mixed and apportioned into individual reactions for the next step of coupling. These approaches yield a stochastic collection of $n^x$ different peptides for screening, where n is the number of building blocks and x is the number of cycles of reaction.

Alternatively, arrays of molecules can be generated in which one or more positions contain known amino acids, while the remainder are random (Gallop et al. Supra). These yield a limited library which is screened for members with the desired activity. These members are identified, their structure determined, and the structure regenerated with another position containing defined amino acids and screened. This iterative approach ultimately yields peptides which are optimal for recognizing the conformational binding pocket of a receptor.

In addition, arrays are not limited to amino acids forming peptides, but can be extended to linear and nonlinear arrays of organic molecules (Gordon et al., 1994 *J. Medicinal Chemistry* 37:1385, which is incorporated herein by reference). Indeed, employing this approach of generating libraries of randomly arrayed inorganic building blocks, ligands which bound to 7-transmembrane receptors were identified (Zuckermann at al., 1994 *J Med Chem.* 37:2678, which is incorporated herein by reference).

Libraries are currently being constructed which can be modified after synthesis to alter the chemical side groups and bonds, to give "designer" arrays to test for their interaction with receptors (Osteresh et al., 1994 *Proc. Natl. Acad. Sci. USA* 91:11138, which is incorporated herein by reference). This technique, generating "libraries from libraries", was applied to the permethylation of a peptide library which yielded compounds with selective antimicrobial activity against gram positive bacteria.

Libraries are also being constructed to express arrays of pharmacological motifs, rather than specific structural arrays of amino acids (Sepetov et al., 1995 *Proc. Natl. Acad. Sc. USA* 92:5426, which is incorporated herein by reference). This technique seeks to identify structural motifs that have specific affinities for receptors, which can be modified in further refinements employing libraries to define structure-activity relationships. Employing this approach of searching motif libraries, generating "libraries of libraries", reduces the number of component members required for screening in the early phase of library examination.

The following is a description of methods of identifying GCC ligands according to the invention from libraries of randomly generated molecules.

Components in the library which interact with receptors may be identified by their binding to receptors immobilized on solid support (Gordon et a. Supra).

They may also be identified by their ability to compete with native ligand for binding to cognate receptors in solution phase (Gordon et al. Supra).

Components may be identified by their binding to soluble receptors when those components are immobilized on solid supports (Gordon et al. Supra).

Once a member of a library which binds receptors has been identified, the structure of that member must be deconvoluted (deduced) in order to identify the structure and generate large quantities to work with, or develop further analogs to study structure-activity relationships. The following is a description of methods of deconvolution for deducing the structure of molecules identified as potential GCC ligands according to the invention.

Peptide libraries may be expressed on the surface of bacteriophage particles (Gallop et al. Supra). Once the peptide interacting with the receptor has been identified, its structure can be deduced by isolating the DNA from the phage and determining its sequence by PCR.

Libraries expressed on plasmids, under the control of the Lac operon can be deconvoluted since these peptides are fused with the lac I protein which specifically interacts with the lac operon on the plasmid encoding the peptide (Gallop et al. Supra) The structure can be deduced by isolating that plasmid attached to the lac I protein and deducing the nucleotide and peptide sequence by PCR.

Libraries expressed on plasmids can also be expressed in cell-free systems employing transcription/translation systems (Gallop et al. Supra). In this paradigm, the protein interacting with receptors is isolated with its attached ribosome and mRNA. The sequence of the peptide is deduced by RT-PCR of the associated mRNA.

Library construction can be coupled with photolithography, so that the structure of any member of the library can be deduced by determining its position within the substrate array (Gallop et al. Supra). This technique is termed positional addressability, since the structural information can be deduced by the precise position of the member.

Members of a library can also be identified by tagging the library with identifiable arrays of other molecules (Ohlmeyer et al., 1993 *Proc. Natl. Acad. Sci. USA* 90:10922, which is incorporated herein by reference, and Gallop et al. Supra). This technique is a modification of associating the peptide with the plasmid of phage encoding the sequence, described above. Some methods employ arrays of nucleotides to encode the sequential synthetic history of the peptide. Thus, nucleotides are attached to the growing peptide sequentially, and can be decoded by PCR to yield the structure of the associated peptide. Alternatively, arrays of small organic molecules can be employed as sequencable tags which encode the sequential synthetic history of the peptide. Thus, nucleotides are attached to the growing peptide sequentially, and can be decoded by PCR to yield the structure of the associated peptide. Alternatively, arrays of small organic molecules can be employed as sequencable tags which encode the sequential synthetic history of the library member.

Finally, the structure of a member of the library can be directly determined by amino acid sequence analysis.

The following patents, which are each incorporated herein by reference, describe methods of making random peptide or non-peptide libraries and screening such libraries to identify compounds that bind to target proteins. As used in the present invention, GCC can be the targets used to identify the peptide and non-peptide ligands generated and screened as disclosed in the patents.

U.S. Pat. No. 5,270,170 issued to Schatz et al. on Dec. 14, 1993, and U.S. Pat. No. 5,338,665 issued to Schatz et al. on Aug. 16, 1994, which are both incorporated herein by reference, refer to peptide libraries and screening methods which can be used to identify GCC ligands.

U.S. Pat. No. 5,395,750 issued to Dillon et al. on Mar. 7, 1995, which is incorporated herein by reference, refers to methods of producing proteins which bind to predetermined antigens. Such methods can be used to produce GCC ligands.

U.S. Pat. No. 5,223,409 issued to Ladner et al. on Jun. 29, 1993, which is incorporated herein by reference, refers to the directed evolution to novel binding proteins. Such proteins may be produced and screened as disclosed therein to identify GCC ligands.

U.S. Pat. No. 5,366,862 issued to Venton et al. on Nov. 22, 1994, which is incorporated herein by reference, refers to methods for generating and screening useful peptides. The methods herein described can be used to identify GCC ligands.

U.S. Pat. No. 5,340,474 issued to Kauvar on Aug. 23, 1994 as well as U.S. Pat. No. 5,133,866, U.S. Pat. No. 4,963,263 and U.S. Pat. No. 5,217,869, which are each incorporated herein by reference, can be used to identify GCC ligands.

U.S. Pat. No. 5,405,783 issued to Pirrung et al. on Apr. 11, 1995, which is incorporated herein by reference, refers to large scale photolithographic solid phase synthesis of an array of polymers. The teachings therein can be used to identify GCC ligands.

U.S. Pat. No. 5,143,854 issued to Pirrung et al. on Sep. 1, 1992, which is incorporated herein by reference, refers to a large scale photolithographic solid phase synthesis of polypeptides and receptor binding screening thereof.

U.S. Pat. No. 5,384,261 issued to Winkler et al. on Jan. 24, 1995, which is incorporated herein by reference, refers to very large scale immobilized polymer synthesis using mechanically directed flow patterns. Such methods are useful to identify GCC ligands.

U.S. Pat. No. 5,221,736 issued to Coolidge et al., on Jun. 22, 1993, which is incorporated herein by reference, refers to sequential peptide and oligonucleotide synthesis using immunoaffinity techniques. Such techniques may be used to identify GCC ligands.

U.S. Pat. No. 5,412,087 issued to McGall et al. on May 2, 1995, which is incorporated herein by reference, refers to spatially addressable immobilization of oligonucleotides and other biological polymers on surfaces. Such methods may be used to identify GCC ligands.

U.S. Pat. No. 5,324,483 issued to Cody et al. on Jun. 28, 1994, which is incorporated herein by reference, refers to apparatus for multiple simultaneous synthesis. The apparatus and method disclosed therein may be used to produce multiple compounds which can be screened to identify GCC ligands.

U.S. Pat. No. 5,252,743 issued to Barrett et al. on Oct. 12, 1993, which is incorporated herein by reference, refers to spatially addressable immobilization of anti-ligands on surfaces. The methods and compositions described therein may be used to identify GCC ligands.

U.S. Pat. No. 5,424,186 issued to Foder et al. on Jun. 13, 1995, which is incorporated herein by reference, refers to a very large scale immobilized polymer synthesis. The method of synthesizing oligonucleotides described therein may be used to identify GCC ligands.

U.S. Pat. No. 5,420,328 issued to Campbell on May 30, 1995, which is incorporated herein by reference, refers to methods of synthesis of phosphonate esters. The phosphonate esters so produced may be screened to identify compounds which are GCC ligands.

U.S. Pat. No. 5,288,514 issued to Ellman on Feb. 22, 1994, which is incorporated herein by reference, refers to solid phase and combinatorial synthesis of benzodiazepine compounds on a solid support. Such methods and compounds may be used to identify GCC ligands.

As noted above, GCC ligands may also be antibodies and fragments thereof. Indeed, antibodies raised to unique determinants of these receptors will recognize that protein, and only that protein and, consequently, can serve as a specific targeting molecule which can be used to direct novel diagnostics and therapeutics to this unique marker. In addition, these antibodies can be used to identify the presence of GCC or fragments there of in biological samples.

The invention claimed is:

1. A method of treating an individual suspected of suffering from primary and/or metastatic stomach or esophageal cancer comprising the step of administering to said individual a therapeutically effective amount of a composition comprising a liposome with an outer liposomal surface that comprises an anti-guanylyl cyclase C antibody which binds to SEQ ID NO:2 associated with the outer liposomal surface and an active agent is encapsulated within the liposome.

2. The method of claim 1 wherein the anti-guanylyl cyclase C antibody is conjugated to the active agent.

3. The method of claim 1 wherein the anti-guanylyl cyclase C antibody and the active agent are unconjugated.

4. The method of claim 1 wherein the anti-guanylyl cyclase C antibody is a monoclonal antibody.

5. The method of claim 1 wherein the anti-guanylyl cyclase C antibody is a FAb or a F(Ab)$_2$.

6. The method of claim 1 wherein the active agent is a therapeutic agent.

7. The method of claim 6 wherein said therapeutic agent is selected from the group consisting of: chemotherapeutics, toxins and radiosensitizing agents.

8. The method of claim 6 wherein said therapeutic agent is selected from the group consisting of: compounds that cause cell death, compounds that inhibit cell division, and compounds that induce cell differentiation.

9. The method of claim 6 wherein said therapeutic agent is selected from the group consisting of: methotrexate, doxorubicin, daunorubicin, cytosinarabinoside, etoposide, 5-fluorouracil, melphalan, chlorambucil, cis-platinum, vindesine, mitomycin, bleomycin, purothionin, macromomycin, 1,4-benzoquinone derivatives, trenimon, ricin, ricin A chain *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, moceccin, viscumin, vokensin, alkaline phosphatase, nitroimidazole, metronidazole, misonidazole, $^{47}$Sc, $^{67}$Cu, $^{90}$Y, $^{109}$Pd, $^{123}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$MPt, $^{197}$Hg, $^{43}$K, $^{52}$Fe, $^{57}$Co, $^{67}$Cu, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi.

10. The method of claim 1 wherein said composition is administered to said individual by injection.

11. The method of claim 1 wherein said composition is administered to said individual intravenously.

12. The method of claim 1 wherein said individual has been diagnosed as having primary esophageal cancer.

13. The method of claim 1 wherein said individual has been diagnosed as having metastatic esophageal cancer.

14. The method of claim 1 wherein said individual has been diagnosed as having primary stomach cancer.

15. The method of claim 1 wherein said individual has been diagnosed as having metastatic stomach cancer.

16. The method of claim 6, wherein said therapeutic agent is a chemotherapeutic agent selected from the group consisting of methotrexate, doxorubicin, daunorubicin, cytosinarabinoside, etoposide, 5-4 fluorouracil, melphalan, chlorambucil, cis-platinum, vindesine, mitomycin, bleomycin, 1,4-benzoquinone derivatives, macromomycin, nitroimidazole, metronidazole, and misonidazole.

17. The method of claim 6, wherein said therapeutic agent is a toxin selected from the group consisting of trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin and purothionin.

18. The method of claim 6, wherein said therapeutic agent is a radiotherapeutic agent selected from the group consisting of $^{47}$Sc, $^{67}$Cu, $^{90}$Y, $^{109}$Pd, $^{123}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{127}$Cs, $^{129}$Cs, $^{132}$I, $^{197}$Hg, $^{203}$Pb and $^{206}$Bi.

\* \* \* \* \*